(12) United States Patent
Qadeer et al.

(10) Patent No.: US 11,959,071 B2
(45) Date of Patent: Apr. 16, 2024

(54) SYSTEMS AND METHODS FOR AUTOMATED NUCLEIC ACID EXTRACTION

(71) Applicant: NTL Biotech, Inc., Skokie, IL (US)

(72) Inventors: Imran Qadeer, Skokie, IL (US); Nicholas Marjanovic, Chicago, IL (US); Zhan Hongliang, Foshan (CN)

(73) Assignee: NTL Biotech, Inc., Skokie, IL (US)

( * ) Notice: Subject to any disclaimer, the term of this patent is extended or adjusted under 35 U.S.C. 154(b) by 0 days.

(21) Appl. No.: 18/364,158

(22) Filed: Aug. 2, 2023

(65) Prior Publication Data
US 2024/0043827 A1     Feb. 8, 2024

Related U.S. Application Data

(60) Provisional application No. 63/394,379, filed on Aug. 2, 2022.

(51) Int. Cl.
*C12N 15/10*     (2006.01)
*B01L 3/00*      (2006.01)

(52) U.S. Cl.
CPC .... *C12N 15/1013* (2013.01); *B01L 3/502761* (2013.01); *B01L 2200/0668* (2013.01);
(Continued)

(58) Field of Classification Search
None
See application file for complete search history.

(56) References Cited

U.S. PATENT DOCUMENTS

| | | | |
|---|---|---|---|
| 8,546,110 B2 * | 10/2013 | Ammann | C12Q 1/6813 435/6.12 |
| 2013/0230860 A1 | 9/2013 | Park et al. | |
| 2020/0131506 A1 | 4/2020 | Vuyisich et al. | |

FOREIGN PATENT DOCUMENTS

| | | | | |
|---|---|---|---|---|
| CN | 107058062 B | | 1/2020 | |
| WO | WO-0060362 A1 * | | 10/2000 | B01L 7/52 |

OTHER PUBLICATIONS

ThermoFisher Scientific, "Your samples, powered by KingFisher instruments: Automated sample preparation for DNA, RNA, protein, or cells," pp. 1-22.

(Continued)

*Primary Examiner* — Matthew D Krcha
*Assistant Examiner* — Brittany I Fisher
(74) *Attorney, Agent, or Firm* — Greenberg Traurig, LLP; Melissa Hunter-Ensor; Kristopher Reichlen

(57) ABSTRACT

Systems and methods of the present disclosure enable automated nucleic acid extraction using components including a rotating platform and a magnetic extractor. A controller controls the components to identify a program associated with a well plate kit based on a well plate kit indicator, where each well plate in the well plate kit is associated with a step for extracting nucleic acid from a sample, and each well plate is loaded with a particular substance for processing each step. Positions on the rotating platform associated with each well plate in the well plate kit are determined. Using the positions and the program, the controller performs each step by determining a particular position for particular well plate of a particular step, controlling the rotating platform to position the particular well plate under the magnetic extractor, and controlling magnetic rods of the magnetic extractor according to the program.

20 Claims, 11 Drawing Sheets

(52) U.S. Cl.
CPC ... *B01L 2300/024* (2013.01); *B01L 2300/025* (2013.01); *B01L 2300/0829* (2013.01)

(56) References Cited

OTHER PUBLICATIONS

Gaddes et al., "Facile Coupling of Droplet Magnetofluidic-Enabled Automated Sample Preparation for Digital Nucleic Acid Amplification Testing and Analysis," Analytical Chemistry, Oct. 2020, vol. 92, No. 19, pp. 13254-13261.

Thakore et al., "A bench-top automated workstation for nucleic acid isolation from clinical sample types," Journal of Microbiological Methods, May 2018, vol. 148, pp. 174-180.

International Search Report and Written Opinion mailed Nov. 20, 2023 in corresponding International PCT Patent Application No. PCT/US2023/071406 (7 pages).

\* cited by examiner

SYSTEMS AND METHODS FOR AUTOMATED NUCLEIC ACID EXTRACTION

CROSS REFERENCE TO RELATED APPLICATION

This application claims priority to and benefit of U.S. Provisional Application No. 63/394,379, filed on Aug. 2, 2022, the entire contents of which are incorporated by reference herein.

BACKGROUND OF THE INVENTION

In fields including deoxyribonucleic acid (DNA) and/or ribonucleic acid (RNA) analysis and engineering, protein analysis and/or engineering, etc., nucleic acid is a fundamental input. The nucleic acid is a basic unit representing genetic characteristics of a subject. The nucleic acid molecule may be analyzed via nucleic acid detection using, e.g., a molecular level biological detection technology. The nucleic acid detection includes technologies such as qualitative polymerase chain reaction (PCR), molecular hybridization, real-time fluorescence quantification PCR and so on. Extracting a nucleic acid from a sample is performed to enable nucleic acid detection.

SUMMARY OF THE INVENTION

As described below, the present disclosure features systems and methods for automated nucleic acid extraction. Embodiments of the present disclosure provide improved sensitivity, reliability and/or repeatability via automated and precise components and control thereof. Other features and advantages of the invention will be apparent from the detailed description, and from the claims.

In some aspects, the techniques described herein relate to a method including: receiving, by a controller, a well plate kit indicator indicative of a plurality of well plates and a sample; wherein each well plate in the plurality of well plates is associated with a step in a plurality of steps for extracting nucleic acid from the sample; wherein each well plate is loaded with a particular substance for processing of the sample according to the plurality of steps; determining, by the controller, a program associated with the well plate kit indicator; wherein the program includes processing parameters defining at least one instruction for performing each step of the plurality of steps; determining, by the controller, a plurality of positions on a rotating platform; wherein each position is associated with a well plate of the plurality of well plates; for each step of the plurality of steps: determining, by the controller, a position of the plurality of positions having a well plate of the plurality of well plates for performing each step; controlling, by the controller, the rotating platform to position the well plate under a magnetic extractor according to the position of the plurality of positions; wherein the magnetic extractor is mounted to a central frame extending through an axis of the rotating platform; controlling, by the controller, at least one actuator associated with the magnetic extractor according to the processing parameters of each step to perform each step on the well plate using a plurality of magnetic rods of the magnetic extractor; and generating, by the controller upon completion of a final step in the plurality of steps, an alert to an operator that the processing of the sample is complete so as to remove the sample.

In some aspects, the techniques described herein relate to a method, further including controlling, by the controller, the rotating platform and the at least one actuator to perform the plurality of steps, including: determining, by the controller, a position of the plurality of array positions associated with each step; controlling, by the controller, the magnetic extractor to extend magnetic rods into a first set of wells of a first well plate associated with a first position of the plurality of positions; controlling, by the controller, the magnetic extractor to perform a mixing step in the first set of wells according to processing parameters associated with the mixing step of the series of steps by actuating the magnetic rods according to at least one first agitation parameter of the mixing step to agitate the sample and cause the sample to mix with the magnetic beads; wherein the magnetic beads are preloaded into the first set of wells; controlling, by the controller, the magnetic extractor and at least one heating element to perform a lysis step in the first set of wells according to processing parameters associated with the lysis step of the series of steps by: actuating the magnetic rods according to at least one second agitation parameter of the lysis step to agitate the sample, and heating the heating element according to heating parameters to heat the sample; controlling, by the controller, the magnetic extractor to perform an extraction step according to processing parameters associated with the extraction step of the series of steps by attracting the magnetic beads to the magnetic rods in the first set of wells; controlling, by the controller, the magnetic extractor to perform a washing step according to processing parameters associated with the washing step of the series of steps; wherein the processing parameters associated with the washing step are configured cause the controller to extract the magnetic rods from the first set of wells and insert the magnetic rods into a second set of wells of a second well plate in a second position associated with washing the magnetic beads; controlling, by the controller, the magnetic extractor to perform an elution step according to processing parameters associated with the elution step of the series of steps; wherein the processing parameters associated with the elution step are configured cause the controller to extract the magnetic rods from the second set of wells and insert the magnetic rods into a third set of wells of a third well plate in a third position associated with eluting the nucleic acid from the magnetic beads; and controlling, by the controller, the magnetic extractor to remove the magnetic rods from the third set of wells to remove the magnetic beads so as to isolate the nucleic acid in the third set of wells.

In some aspects, the techniques described herein relate to a method, further including: controlling, by the controller, the magnetic extractor to perform a deposition step of the series of steps according to processing parameters associated with the deposition step of the series of steps; wherein the series of steps further includes the deposition step for depositing the magnetic beads in the first set of wells; wherein the processing parameters associated with the deposition step are configured cause the controller to control the magnetic extractor to: extend the magnetic rods into the first set of wells, and agitate the magnetic rods to remove the magnetic beads from the magnetic rods so as to deposit the magnetic beads into the first set of wells.

In some aspects, the techniques described herein relate to a method, further including: controlling, by the controller, at least one ultraviolet lamp to irradiate the magnetic extractor and the rotating platform according to disinfection parameters; wherein the disinfection parameters includes an irradiation duration configured to disinfect irradiated surfaces.

In some aspects, the techniques described herein relate to a method, further including receiving, by the controller, the processing parameters by user selection via an input interface.

In some aspects, the techniques described herein relate to a method, wherein the well plate kit includes a pre-loaded well kit.

In some aspects, the techniques described herein relate to a method, further including: receiving, by the controller, a second well plate kit indicator indicative of a second plurality of well plates and a second sample; wherein each well plate in the plurality of well plates is associated with a step in a second plurality of steps for extracting a second nucleic acid from the second sample; wherein each well plate is loaded with a particular substance for processing of the sample according to the plurality of steps; determining, by the controller, a second program associated with the second well plate kit indicator; wherein the second program includes second processing parameters defining at least one second instruction for performing each step of the second plurality of steps; determining, by the controller, a plurality of second positions on the rotating platform; wherein each second position is associated with a well plate of the second plurality of well plates; wherein each second position is adjacent to a respective position of the plurality of positions so as to enable processing two well plate kits in parallel.

In some aspects, the techniques described herein relate to a method, wherein the magnetic rods include non-magnetic sleeves; and wherein the controller controls the at least one actuator to separately actuate the magnetic rods and the non-magnetic sleeves.

In some aspects, the techniques described herein relate to a method, further including controlling, by the controller, a second heater at a second position of the rotating platform to pre-heat at least one well plate of the plurality of well plates.

In some aspects, the techniques described herein relate to a method, wherein each position is associated with two well plates of two well plate kits; wherein the magnetic extractor includes two sets of magnetic rods; and wherein each set of magnetic rods of the two sets of magnetic rods are independently controllable to process a respective well plate of the two well plates of each position.

In some aspects, the techniques described herein relate to a system including: a controller of an automated nucleic acid extractor, wherein the controller is configured to: receive a well plate kit indicator indicative of a plurality of well plates and a sample; wherein each well plate in the plurality of well plates is associated with a step in a plurality of steps for extracting nucleic acid from the sample; wherein each well plate is loaded with a particular substance for processing of the sample according to the plurality of steps; determine a program associated with the well plate kit indicator; wherein the program includes processing parameters defining at least one instruction for performing each step of the plurality of steps; determine a plurality of positions on a rotating platform; wherein each position is associated with a well plate of the plurality of well plates; for each step of the plurality of steps: determine a position of the plurality of positions having a well plate of the plurality of well plates for performing each step; control the rotating platform to position the well plate under a magnetic extractor according to the position of the plurality of positions; wherein the magnetic extractor is mounted to a central frame extending through an axis of the rotating platform; control at least one actuator associated with the magnetic extractor according to the processing parameters of each step to perform each step on the well plate using a plurality of magnetic rods of the magnetic extractor; and generate, upon completion of a final step in the plurality of steps, an alert to an operator that the processing of the sample is complete so as to remove the sample.

In some aspects, the techniques described herein relate to a system, wherein the controller is further configured to control the rotating platform and the at least one actuator to perform the plurality of steps, including: determine a position of the plurality of array positions associated with each step; control the magnetic extractor to extend magnetic rods into a first set of wells of a first well plate associated with a first position of the plurality of positions; control the magnetic extractor to perform a mixing step in the first set of wells according to processing parameters associated with the mixing step of the series of steps by actuating the magnetic rods according to at least one first agitation parameter of the mixing step to agitate the sample and cause the sample to mix with the magnetic beads; wherein the magnetic beads are preloaded into the first set of wells; control the magnetic extractor and at least one heating element to perform a lysis step in the first set of wells according to processing parameters associated with the lysis step of the series of steps by: actuating the magnetic rods according to at least one second agitation parameter of the lysis step to agitate the sample, and heating the heating element according to heating parameters to heat the sample; control the magnetic extractor to perform an extraction step according to processing parameters associated with the extraction step of the series of steps by attracting the magnetic beads to the magnetic rods in the first set of wells; control the magnetic extractor to perform a washing step according to processing parameters associated with the washing step of the series of steps; wherein the processing parameters associated with the washing step are configured cause the controller to extract the magnetic rods from the first set of wells and insert the magnetic rods into a second set of wells of a second well plate in a second position associated with washing the magnetic beads; control the magnetic extractor to perform an elution step according to processing parameters associated with the elution step of the series of steps; wherein the processing parameters associated with the elution step are configured cause the controller to extract the magnetic rods from the second set of wells and insert the magnetic rods into a third set of wells of a third well plate in a third position associated with eluting the nucleic acid from the magnetic beads; and control the magnetic extractor to remove the magnetic rods from the third set of wells to remove the magnetic beads so as to isolate the nucleic acid in the third set of wells.

In some aspects, the techniques described herein relate to a system, wherein the controller is further configured to: control the magnetic extractor to perform a deposition step of the series of steps according to processing parameters associated with the deposition step of the series of steps; wherein the series of steps further includes the deposition step for depositing the magnetic beads in the first set of wells; wherein the processing parameters associated with the deposition step are configured cause the controller to control the magnetic extractor to: extend the magnetic rods into the first set of wells, and agitate the magnetic rods to remove the magnetic beads from the magnetic rods so as to deposit the magnetic beads into the first set of wells.

In some aspects, the techniques described herein relate to a system, wherein the controller is further configured to: control at least one ultraviolet lamp to irradiate the magnetic extractor and the rotating platform according to disinfection parameters; wherein the disinfection parameters include an irradiation duration configured to disinfect irradiated surfaces.

In some aspects, the techniques described herein relate to a system, wherein the controller is further configured to receive the processing parameters by user selection via an input interface.

In some aspects, the techniques described herein relate to a system, wherein the well plate kit includes a pre-loaded well kit.

In some aspects, the techniques described herein relate to a system, wherein the controller is further configured to: receive a second well plate kit indicator indicative of a second plurality of well plates and a second sample; wherein each well plate in the plurality of well plates is associated with a step in a second plurality of steps for extracting a second nucleic acid from the second sample; wherein each well plate is loaded with a particular substance for processing of the sample according to the plurality of steps; determine a second program associated with the second well plate kit indicator; wherein the second program includes second processing parameters defining at least one second instruction for performing each step of the second plurality of steps; determine a plurality of second positions on the rotating platform; wherein each second position is associated with a well plate of the second plurality of well plates; wherein each second position is adjacent to a respective position of the plurality of positions so as to enable processing two well plate kits in parallel.

In some aspects, the techniques described herein relate to a system, wherein the magnetic rods include non-magnetic sleeves; and wherein the controller controls the at least one actuator to separately actuate the magnetic rods and the non-magnetic sleeves.

In some aspects, the techniques described herein relate to a system, wherein the controller is further configured to control a second heater at a second position of the rotating platform to pre-heat at least one well plate of the plurality of well plates.

In some aspects, the techniques described herein relate to a system, wherein each position is associated with two well plates of two well plate kits; wherein the magnetic extractor includes two sets of magnetic rods; and wherein each set of magnetic rods of the two sets of magnetic rods are independently controllable to process a respective well plate of the two well plates of each position.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "lysis" is meant the disintegration of a cell by rupture of the cell wall or membrane via a suitable sample processing technique, such as, by osmosis via introduction of another substance such as by an enzyme or detergent or other chaotropic agents.

By "chaotropic agent" is meant a molecule in water solution that can disrupt the hydrogen bonding network between water molecules.

By "elution" and/or "elute" and/or "eluting" is meant a process to remove (an adsorbed substance) by washing with a solvent.

By "agent" is meant a peptide, nucleic acid molecule, or small compound.

By "ameliorate" is meant decrease, suppress, attenuate, diminish, arrest, or stabilize the development or progression of a disease.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical but has analogous functional or structural features. For example, a polypeptide analog retains the biological activity of a corresponding naturally occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "includes," "including," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence, or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include [insert]

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2-base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

By "subject" is meant a mammal, including, but not limited to, a human or non-human mammal, such as a bovine, equine, canine, ovine, or feline.

By "sample" is meant any substance having cells from which nucleic acids may be extracted, such as blood, serum, plasma, cerebrospinal fluid (CSF), tears, sputum, saliva, stool, urine, synovial fluid, cells, tissues, organs, bronchial gavage specimen, peritoneal fluid, bacteria, viruses, or any other nucleic acid containing biological materials from micro-organism, bacterial, plant, animal and/or human biological material, whether suspended in a fluid or otherwise. Sample may refer to cells, cells that encompass normal cells, cell lines, transformed cells, cancer/tumor/neoplastic cells, bone marrow cells, and/or cells from most any source in an organism.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

The term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

The term "runtime" corresponds to any behavior that is dynamically determined during an execution of a software application or at least a portion of software application.

The term "user interface" refers to a point of interaction between a computer and humans, including any number of modalities of interaction (such as graphics, sound, position, movement, etc.) where data is transferred between the user and the computer system.

The term "graphical user interface" refers to a form of user interface that allows users to interact with electronic devices through graphical elements and audio indicator such as primary notation, instead of text-based UIs, typed command labels or text navigation.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

The term "hardware elements" may include memory devices, processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

The term "processor" may include any type of data processing capacity, such as a hardware logic circuit, for example an application specific integrated circuit (ASIC) and a programmable logic, or such as a computing device, for example, a microcomputer or microcontroller that include a programmable microprocessor.

The term "memory device" may include a suitable memory or storage solutions for maintaining electronic data representing the activity histories for each account. For example, the data storage solution may include database technology such as, e.g., a centralized or distributed database, cloud storage platform, decentralized system, server, or server system, among other storage systems. In some embodiments, the data storage solution may, additionally or alternatively, include one or more data storage devices such as, e.g., a hard drive, solid-state drive, flash drive, or other suitable storage device. In some embodiments, the data storage solution may, additionally or alternatively, include one or more temporary storage devices such as, e.g., a random-access memory, cache, buffer, or other suitable memory device, or any other data storage solution and combinations thereof.

The term "database" refers to an organized collection of data, stored, accessed or both electronically from a computer system. The database may include a database model formed by one or more formal design and modeling techniques. The database model may include, e.g., a navigational database, a hierarchical database, a network database, a graph database, an object database, a relational database, an object-relational database, an entity-relationship database, an enhanced entity-relationship database, a document database, an entity-attribute-value database, a star schema database, or any other suitable database model and combinations thereof. For example, the database may include database technology such as, e.g., a centralized or distributed database, cloud storage platform, decentralized system, server, or server system, among other storage systems. In some embodiments, the database may, additionally or alternatively, include one or more data storage devices such as, e.g., a hard drive, solid-state drive, flash drive, or other suitable storage device. In some embodiments, the database may, additionally or alternatively, include one or more temporary storage devices such as, e.g., a random-access memory, cache, buffer, or other suitable memory device, or any other data storage solution and combinations thereof.

The term "software" may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session or can refer to an automated software application which receives the data and stores or processes the data.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION OF THE INVENTION

FIGS. 1 through 10 illustrate systems and methods of automated nucleic acid extraction. Typically, nucleic acid extraction is performed under manual control and/or with preparation and post-processing performed independently from the extraction process. Such techniques introduce error and inconsistency, in addition to increased time processing the sample and reduced efficiency. The following embodiments provide technical solutions and technical improvements that overcome technical problems, drawbacks and/or deficiencies in the technical fields involving insufficiently reliable, precise, and repeatable extraction of nucleic acid molecules from a sample. As explained in more detail, below, technical solutions and technical improvements herein include aspects of improved standardization and precision of sample preparation and processing for nucleic acid extraction by leveraging automated components for end-to-end automation of the sample preparation and processing for automated nucleic acid extraction.

Based on such technical features, further technical benefits become available to users and operators of these systems and methods. Moreover, various practical applications of the disclosed technology are also described, which provide further practical benefits to users and operators that are also new and useful improvements in the art.

Figure 1:
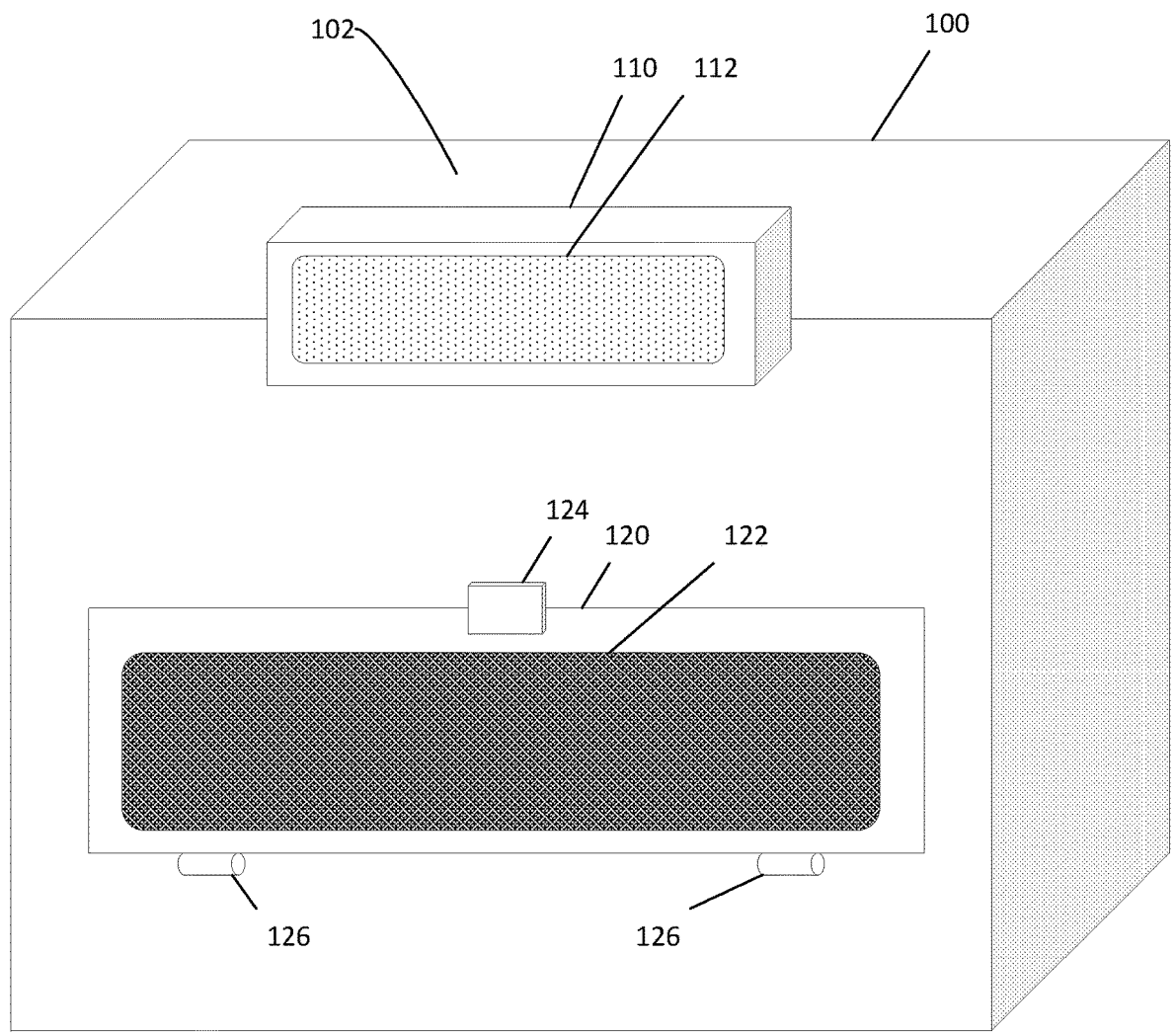
FIG. 1 depicts an illustration of an exterior view an automated nucleic acid extractor for inserting one or more samples and automatically performing nucleic acid extraction on the one or more samples according to one or more programs in accordance with one or more embodiments of the present disclosure.

Referring to FIG. 1, an exterior view is illustrated an automated nucleic acid extractor for inserting one or more samples and automatically performing nucleic acid extraction on the one or more samples according to one or more programs in accordance with one or more embodiments of the present disclosure.

In some embodiments, an automated nucleic acid extractor 100 is configured to receive, manipulate, and process samples in order to precisely and reliably extract nucleic acids for improved repeatability and accuracy. In some embodiments, the automated nucleic acid extractor 100 includes an exterior housing 102 that encloses an interior. In some embodiments, the exterior housing 102 is made of a stainless-steel plate with a thickness of 0.1-2.0 mm processed and manufactured by techniques such as cold rolling, cold cutting and so on. In some embodiments, the exterior housing 102 may be made of a plastic material manufactured by injection molding to reduce the cost. A plurality of mutually parallel or crisscross tendons or ribs may be designed on the exterior housing 102 to improve the strength of the exterior housing 102. In some embodiments, the exterior housing 102 may be treated by techniques such as paint spraying, computer inkjet, computer carving, etching, electroplating and so on, so that the outer housing has a better appearance.

In some embodiments, a side of the exterior housing 102 facing an operator, i.e., the front side of the automated nucleic acid extractor 100, may include an access door 120, that when in an open position, presents an opening in the exterior housing 102 providing access to the interior. In some embodiments, the access door 120 may be attached to the exterior housing 102 with a suitable attachment mechanism, such as, e.g., one or more latches, clasps, hinges, brackets, hooks, toggles, hook-and-loop closures, fasteners, among others or any suitable combination thereof. In some embodiments, the attachment mechanisms may include hinges 126 and a latch 124. The hinges 126 may attach an edge of the access door 120 (e.g., a bottom edge of the access door 120 or any suitable edge) in a rotatable fashion to the exterior housing 102. When in a closed position, the latch 124 may releasably secure an edge of the access door 120 to the exterior housing 102 such that the access door 120 is maintained in the closed position until the latch 124 is manipulated to unlatch or release the edge of the access door 120 from the exterior housing 102.

In some embodiments, to facilitate the operator monitoring sample processing and/or identifying faults or errors or both, the access door may include a transparent window 122. The transparent window 122 may include, e.g., a suitable transparent material that is resistant to corrosion and/or failure under the temperature and environment within the automated nucleic acid extractor 100 during processing of the sample. For example, the transparent window 122 may include, e.g., any suitable transparent polymer (e.g., polycarbonate, acrylic, polyethylene terephthalate (PET), amorphous copolyester (PETG), polyvinyl chloride (PVC), liquid silicone rubber (LSR), polyethylene (PE), cyclic olefin copolymer, ionomer resin, transparent polypropylene (PP), fluorinated ethylene propylene (FEP), styrene methyl methacrylate (SMMA), styrene acrylonitrile resin (SAN), general purpose polystyrene (GPPS), methyl methacrylate acrylonitrile butadiene styrene (MABS), etc.), glass, sapphire, borosilicate, a transparent ceramic, a transparent metal, or any other suitable window material or any combination thereof.

In some embodiments, the front of the automated nucleic acid extractor 100 may include a control device 110. In some embodiments, the control device 110 may include a suitable computer and/or processing device configured to control each component of the automated nucleic acid extractor 100 to perform nucleic acid extraction-related processes on a sample. In some embodiments, the computer and/or processing device may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

In some embodiments, the control device 110 may include one or more hardware elements for executing software instructions. In some embodiments, the hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Similarly, the control device 110 may include storage, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the storage may include, e.g., a suitable non-transient computer readable medium such as, e.g., random access memory (RAM), read only memory (ROM), one or more buffers and/or caches, among other memory devices or any combination thereof.

In some embodiments, the control device 110 may implement computer engines for executing one or more sample processing steps related to nucleic acid extraction. In some embodiments, the sample processing steps may include, e.g., controlling a mixing sleeve for mixing one or more substances with the sample and/or performing lysis, controlling magnetic implements magnetically extract the nucleic acid and/or washing the magnetic implements in disinfecting fluids, controlling heating elements and/or ventilation for heating and/or temperature control and/or environmental control, controlling ultraviolet lamps for disinfection (of the sample and/or interior of the automated nucleic acid extractor 100), among other steps or any combination thereof.

In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.). The computer engines of the control device 110 may include one or more computer engines that in combination or individually perform each step of the sample processing for automated nucleic acid extraction.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the control device 110 may include a suitable interface mechanism to enable a user to input selections, text, numerical values, or otherwise perform manual control and configuration of the automated nucleic acid extractor 100. In some embodiments, the interface mechanism may include a display panel 112 that renders a user interface (UI), such as a graphical user interface (GUI), command line interface (CLI), or other suitable visual user interface. In some embodiments, the interface mechanism may include elements for user input to interact with the UI, such as, e.g., a mouse, keyboard, operating keys/buttons/switches, touch-sensitive panel integrated with the display panel 112, touch-sensitive panel separate from the display panel 112, stylus, motion tracking, voice and/or speech recognition (e.g., artificial intelligence-based voice assistants such as, e.g., Amazon® Alexa, Apple® Siri®, Google® Assistant, etc.), among other user input elements or any combination thereof.

In some embodiments, using the display panel 112, the operator may interact with the control device 110 to configure nucleic acid extraction programs, including adding new programs to a library, editing programs within the library, removing programs from the library, performing error detection, performing device calibration, or otherwise instructing and/or configuring the automated nucleic acid extractor 100.

Figure 2A:
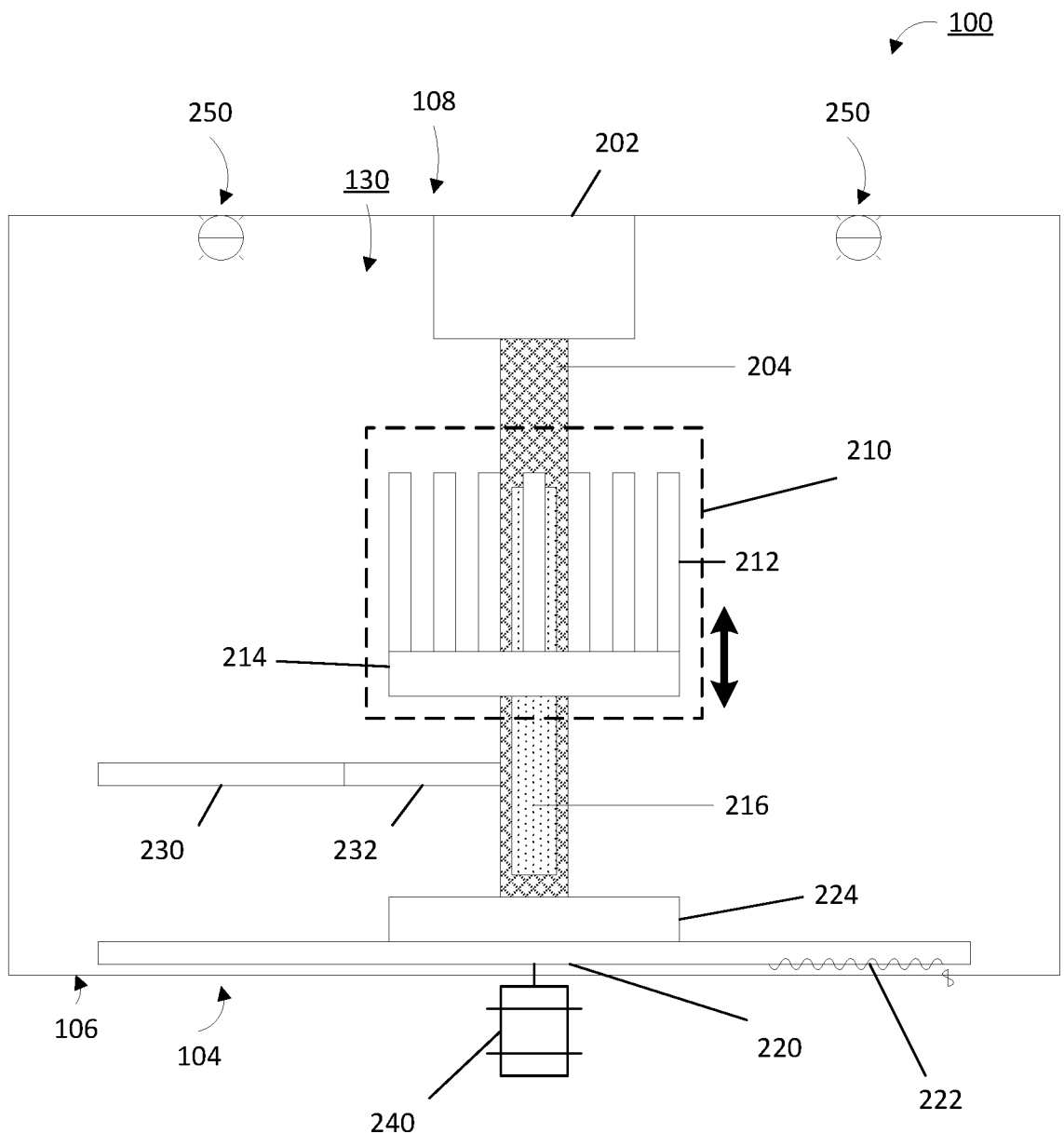
FIG. 2A and FIG. 2B depict an interior view of components of the automated nucleic acid extractor for inserting one or more samples and automatically performing nucleic acid extraction on the one or more samples according to one or more programs in accordance with one or more embodiments of the present disclosure.
Figure 2B:
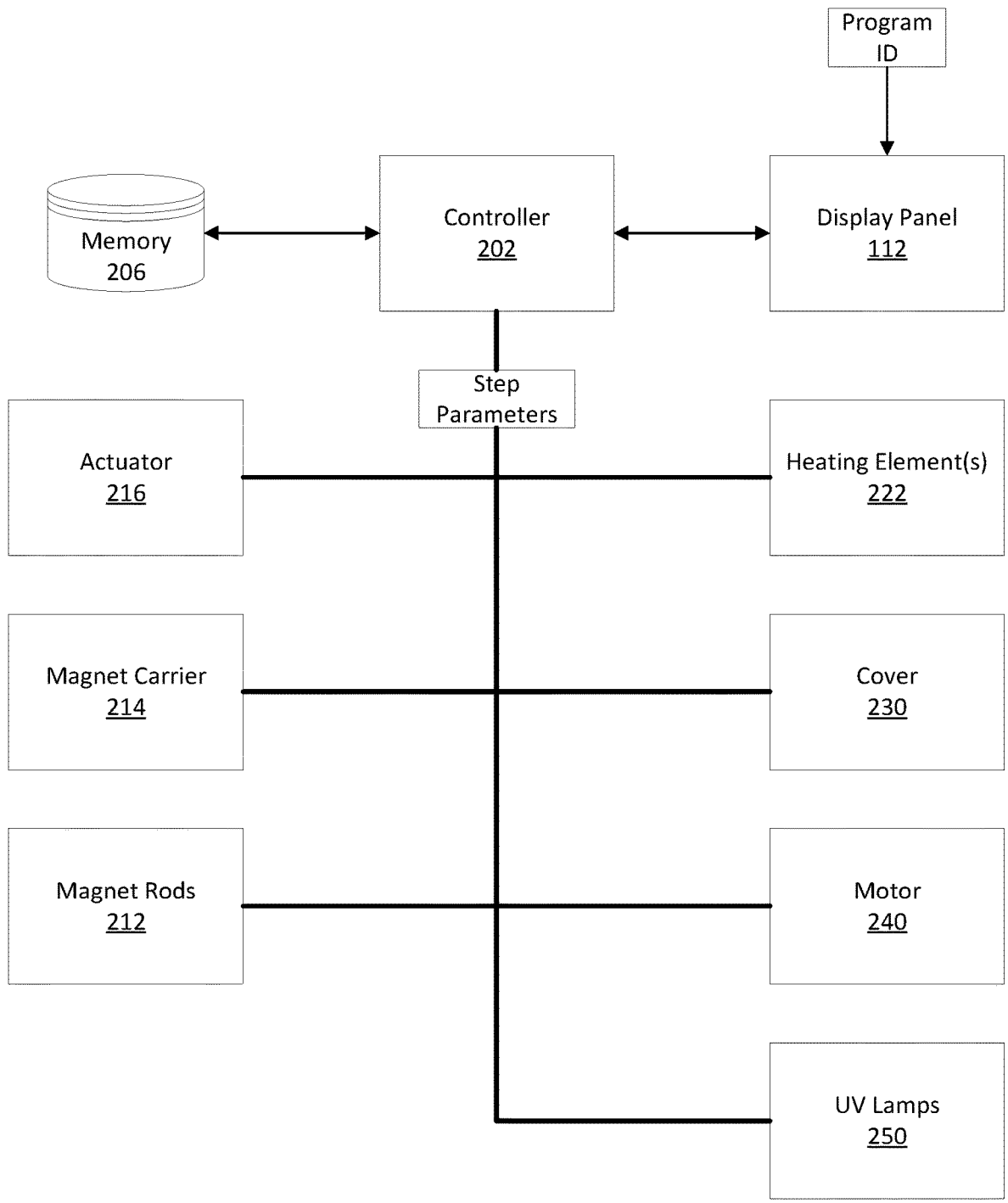

Referring to FIG. 2, an interior view is illustrated of components of the automated nucleic acid extractor for inserting one or more samples and automatically performing nucleic acid extraction on the one or more samples according to one or more programs in accordance with one or more embodiments of the present disclosure.

In some embodiments, the automated nucleic acid extractor 100 may have an interior 130 enclosed by sidewalls 106, a base 104 and a top wall 108. In some embodiments, one or more of the sidewalls 106, the base 104 and the top wall 108 may be part of the exterior housing 102. In some embodiments, one or more of the sidewalls 106, the base 104 and the top wall 108 may be part of an interior housing within the exterior housing and enclosing the interior 130.

In some embodiments, one or more of the sidewalls 106, the base 104 and the top wall 108 may be made of a material (such as cast iron, steel, a concrete-filled steel plate and so on) with relatively high specific weight and low cost, so that the base has a relatively high mass, thereby effectively preventing the nucleic acid extraction instrument from agitating and moving while operating. In some embodiments, one or more of the sidewalls 106, the base 104 and the top wall 108 may be formed from a lighter and/or cheaper material, such as, e.g., a polymer, fiberglass, etc. where agitation dampening is not a concern (e.g., when other structural reinforcements are employed, using dampener components such as bushings, or in environments where agitation is unlikely to affect the automated nucleic acid extractor 100, among others or any combination thereof).

In some embodiments, within the interior 130, the automated nucleic acid extractor 100 may include a rotating platform 220 and a central frame 204 about which the rotating platform 220 may rotate. In some embodiments, well plates may be positioned on the rotating platform 220 within one or more well plate carriers 224. The well plate carrier(s) 224 includes one or more securing mechanisms such as, e.g., one or more brackets, protrusions, detents, recesses, or other structures or any combination thereof configured to mate with the well plate and secure the well plate in position on the rotating platform 220.

In some embodiments, the rotating platform 220 enables the well plate in the well plate carrier 224 to be repositioned within the automated nucleic acid extractor 100. Thus, the rotating platform 220 can bring a well plate into a position to be processed by one or more instruments. As a result, various processes can be performed on the samples in the well plate by move the well plate carrier 224 into position to be processed by the associated instrument. Such instruments may include, e.g., a magnetic extractor 210, a heating element 222, a cover 230, among other instruments such as, e.g., a sample agitator, mixing sleeve, a dispenser (e.g., for dispensing a reagent, a reactant, a solvent, a catalyst, a substrate, or other substance or any combination thereof), or any combination thereof.

In some embodiments, rotation of the rotating platform 220 may be performed by a motor 240 under the control of a controller 202. In some embodiments, the controller 202 may include the hardware and/or software elements of the control device 110, such as, e.g., one or more processing devices, memory 206 devices, computer engines, etc. In some embodiments, based on the program for processing the sample of the well plate in the well plate carrier 224, the controller 202 may control the motor 240 to position the well plate carrier 224 within reach of an instrument associated with a current step of the program.

In some embodiments, the motor 240 may include any suitable electric motor. The electric motor may be powered by direct current (DC) sources, such as from batteries, or rectifiers, or by alternating current (AC) sources, such as a power grid, inverters, or electrical generators. For example, the motor 240 may a DC motor power by a battery and/or rectified AC power from the power grid (e.g., 120 volt (V) and/or 240 V power outlet). In another example, the motor 240 may be an AC motor power directly by the power grid and/or an inverted DC power source (e.g., battery). In some embodiments, the electric motor may be brushed or brushless, single-phase, two-phase, or three-phase, axial or radial flux, and may be air-cooled or liquid-cooled.

In some embodiments, the motor 240 may be mounted to the base 104 with the axle parallel to the rotational axis of the rotating platform 220. In some embodiments, the motor 240 may be mounted to the base 104 with the axle perpendicular to the rotational axis of the rotating platform 220 (e.g., parallel to a plane across which the rotating platform 220 extends). In some embodiments, the motor 240 may have a rotating axle that interfaces with the rotating platform 220 via a gear and/or gear system, via belt drive, via friction at a wheel on the axle, or by any other suitable drive unit enabling the transfer of rotational force from the axle of the motor 240 to the drive the rotation of the rotating platform 220.

In some embodiments, the controller 202 may control the motor 240 to bring the well plate carrier 224 into a position of an instrument for performing a step in a program of processing a sample. In some embodiments, the instruments may include a magnetic extractor 210. The magnetic extractor 210 may be configured to provide magnetic separation of the nucleic acid in the sample, as well as to perform one or more other steps, such as sample agitation, mixing, lysing or others or any combination thereof.

In some embodiments, the magnetic extractor 210 has an array of magnetic rods 212 mounted on a magnet carrier 214. The magnet carrier 214 is mounted to the central frame 204 and is moved up the central frame 204 towards the top wall 108 and/or down the central frame 204 toward to the well plate carrier 224 via an actuator 216. For example, the magnet carrier 214 may be fixedly connected to a sliding block of the actuator 216 and the magnetic rods 212 may be fixedly connect to an actuator of the magnet carrier 214.

In some embodiments, the controller 202 may control the motor 240 to rotate the rotating platform 220 to bring the well plate carrier 224 to a position under the magnet carrier 214. In some embodiments, upon positioning the well plate carrier 224, the controller 202 may control the actuator 216 to move the magnetic extractor 210 downward toward to a well plate in the well plate carrier 224 to bring the magnetic rods 212.

In some embodiments, the magnetic rods 212 in the magnet carrier 214 may be positioned in an arrangement that matches an arrangement of wells in the well plate. For example, the well plate may include a 24-will plate, a 96 well plate, a 192 well plate, or any other size well plate having an array of wells. In some embodiments, the well plate carrier 224 may be configured to accept and retain multiple well plates, such as, e.g., two well plates, three well plates, four well plates, etc., where each well plate is of a same or different size. The array of magnetic rods 212 may align with the array of wells in each well plate such that the magnetic rods 212 may be vertically repositioned to be inserted into corresponding wells in the well plate.

In some embodiments, the controller 202 may control the magnetic extractor 210 to run a process that includes receiving one or more well plates. When the automated nucleic acid extractor 100 is in a starting position, the magnet carrier 214 is separated from the magnet carrier 214 and is spaced a sufficiently large distance from the rotating platform 220. The automated nucleic acid extractor 100 in the present invention sequentially runs according to the following steps:

One or more well plates (such as a 24-well plate, 96-well plate, 192-well plate, etc.) are placed at the well plate carrier 224 of the rotating platform 220. In some embodiments, the well plate(s) may be pre-filled with one or more fluids for lysis, washing, elution and/or any other suitable nucleic acid extraction steps. In some embodiments, the fluids may be specific to the sample being processed, such as, e.g., a viral sample, bacterial sample, biological fluid sample, among others or any combination thereof. In some embodiments, the well plate(s) may be positioned in a specific position on the rotating platform 220 having an associated well plate carrier 224. In some embodiments, the positions on the rotating platform 220 may include a number of positions associated with a number of steps used for nucleic acid extraction, such as, e.g., 3, 4, 5, 6, 7, 8 or more positions. Each position may be associated with a well-plate carrier 224 located at regular angular intervals around the rotating platform 220 such that the rotating platform 220 may rotated to selectively position each well plate under the magnet carrier 210 according to a current processing step.

The motor 240 may drive the rotating platform 220 to bring a first, lysis well plate into position below the magnetic extractor 210 for a first processing step for nucleic acid extraction.

The actuator 216 may position the magnet carrier 214 in proximity to the well plate in the well plate carrier 224.

In some embodiments, an agitation portion 216 of the magnetic rods 212 may descend in corresponding wells in the well plate, e.g., via actuation of the actuator 216, an actuator driving the agitation portion 216 of the magnetic rods 212 on magnet carrier 214, and/or individual actuators in the magnet carrier 214 associated with each magnetic rod 212 to drive the agitation portion 216 of each magnetic rod 212. In some embodiments, the actuator, whether the actuator 216 or other actuator, may drive the agitation portion 216 of the magnetic rods 212 to oscillate the vertically to agitate the sample in the wells of the well plate. In some embodiments, any other suitable mechanism may be included in the magnet carrier 214 may include one or more agitation devices that cause the agitation portion 216 of the magnetic rods 212 to agitate or otherwise move to cause agitation of the sample in each well in the well plate, such as by horizontal and/or circular oscillation, vertical oscillation, vibration, or any combination thereof. Such agitation may be used to perform mixing and/or lysing. In some embodiments, the agitation may include, e.g., driving the magnet carrier 214 and the magnetic rods 212 together to agitate for a preset time according to a frequency including, e.g., 2 Hz, 4 Hz, 8 Hz, 16 Hz, 21 Hz, 30 Hz, 50 Hz, 80 Hz, or 100 Hz, or other suitable frequency in a range from 2 through 100 Hz.

In some embodiments, the agitation portion 216 used to agitate the sample may be a sleeve around each magnetic rod 212, a non-magnetic rod parallel to each magnetic rod 212, or other suitable portion or any combination thereof. In some embodiments, the agitation portion 216 may be actuated separately from the magnetic rods 212 such that the agitation portion 216 may be inserted into the wells without inserting the magnetic rods 212. In some embodiments, where a sleeve is used, at a step for removing magnetic beads from the magnetic rods 212, as is described in further detail below, the sleeve may be actuated to descend to a position of the magnetic rods 212 thus scraping the magnetic beads off of the magnetic rods 212.

In some embodiments, to lyse the sample, the agitation portion 216 the magnet bars 212 may be inserted into wells to stir a mixture of the sample, a lysing solution, and magnetic beads (placed in the wells of the deep well plate in advanced) in the wells of the well plate, so that nucleic acid in the sample is separated from the sample (that is, the nucleic acid is lysed) and adsorbed on the magnetic beads.

The actuator 216 is controlled to drive the magnet carrier 214 to position the magnetic rods 212 in specified positions to rest for a preset time, so that all the magnetic beads are attracted on outer surfaces of the magnetic rods 212 together with the nucleic acid lysed from the sample. The actuator 216 may then be controlled to lift the magnet carrier 214 and the magnetic rods 212 to lift the magnetic rods 212 from the wells of the well plate.

In some embodiments, the magnetic rods 212 may first lyse a subset of the wells in the well plate. For example, the well plate may be organized into multiple positions, e.g., according to row, column, or other division of the array of wells in the well plate.

Thus, upon lifting the magnetic rods 212 from the wells in the position of the well plate for lysing and extraction, the rotating platform 220 and the actuator 216 are controlled bring a next, washing well plate into position. Upon entering the second position, the actuator 216 and/or the magnet carrier 214 may lower the magnetic rods 212 into the wells of the second position. In some embodiments, the wells of the second position may include washing wells for washing the magnetic rods 214 to remove impurities. In some embodiments, washing may be performed multiple times with the same or different washing solution. Each washing step may be performed in a separate well plate with the same or different washing solution. Accordingly, for washing step the magnetic rods 212 may be removed from the well plate, and the rotating platform 220 rotated to bring another washing position having another washing well plate into position beneath the magnet carrier 210.

The actuator 216 and/or the magnet carrier 214 may be controlled to lift the magnet carrier 214 and the magnetic rods 212 from the second position so that the rotating platform 220 may being a third, eluting position including bringing an eluting well plate below the magnet carrier 214. The actuator 215 and/or the magnet carrier 214 may be controlled to insert the magnetic rods 212 into the eluting wells. In some embodiments, the eluting wells may include an eluting solution to cause the nucleic acid to be released from the magnetic beads. In some embodiments, the eluting solution may include, e.g., free water or other suitable fluid for eluting nucleic acid.

The magnetic beads attracted on the outer surfaces of the magnetic rods 212 may be transferred into magnetic bead recovery wells from the eluting wells. To do so, the actuator 216 and/or the magnet carrier 214 may be controlled to remove the magnetic rods 212 from the eluting wells so that the rotating platform 220 may being a fourth, recovery position including bringing a recovery well plate below the magnet carrier 214. The actuator 215 and/or the magnet carrier 214 may be controlled to insert the magnetic rods 212 into the recovery wells. In some embodiments, the recovery wells may be in the first, lysis well plate in order to reduce waste and save space on rotating platform.

To remove the magnetic beads, the actuator 216 and/or magnet carrier 214 may be controlled to actuate the agitation portion 216 including a sleeve to slide across a surface of the magnetic rods 212 thereby scraping the magnetic beads of the magnetic rods 212 into magnetic bead recovery wells. In some embodiments, the magnet carrier may be controlled to agitate the magnetic rods 212 in the magnetic bead recovering wells, so that the magnetic beads fall off from the outer surfaces of the magnetic rods 212. Any other suitable mechanism for removing the magnetic beads from the magnetic rods 212 may be employed or any combination thereof.

Upon extracting the nucleic acid and removing the magnetic beads, the magnetic extractor 210 may be repositioned to the original starting position, the operator may remove the well plate, and the controller 202 may operate ultraviolet lamps 250 to disinfect the interior 130 and the instruments within the interior to prevent cross-contamination.

In some embodiments, during loading of a well plate and/or unloading of well plate after completion of the nucleic acid extraction program, the cover 230 may move into place between the magnetic extraction 210 and the well plate carrier 224. In some embodiments, the central frame 204 may include a drive mechanism, such as a motor, linear actuator, rotational actuator, or other drive mechanism connected to a cover mount arm 232. In some embodiments, before a program commences, after a program completes and/or upon an operator opening the access door 120, the controller 202 may control the drive mechanism to rotate the cover mount arm 232 around the central frame 206 to position the cover 230 over the well plate to prevent splatter of the substances in the well plate. Thus, a risk of cross contamination can be reduced by automatic control of the cover 230.

In some embodiments, the controller 202 may execute customized programs based on operator selection. A program may include parameters for each step in a sequence of steps including, e.g., (1) mixing a reagent and/or magnetic beads with the sample, (2) lysing the sample, (3) extracting the magnetic beads with nucleic acids using the magnetic rods 214, (4) washing the magnetic rods 214 and magnetic beads, (5) eluting the nucleic acid from the magnetic beads, (6) removing the magnetic rods 212 with the magnetic beads, (7) depositing the magnetic beads, and (8) disinfecting the interior 130. In some embodiments, each step of the program may include parameters such as duration and other control parameters. Thus, a program may be defined by the steps of the program and the parameters of each step.

In some embodiments, the program may be created by the operator, e.g., via the display panel 112 of the control device 110 by the operator selecting the steps and the parameters of each step via the UI. The operator may store the program in the memory 206 of the control device 110 to add the program to a library of programs. In some embodiments, the library of programs may include one or more operator defined programs or predefined programs or both.

Each program in the library may be associated with a particular reagent, reagent kit, sample, or other feature of the nucleic acid extraction. Thus, each program may be linked to, named according to, defined with an identifier that matches to, and/or has a description matching to the particular reagent, reagent kit, sample, or other feature of the nucleic acid extraction to which each program is associated. For example, the programs may be indexed in a look-up table or index that maps each program to the associated reagent, reagent kit, sample, or other feature of the nucleic acid extraction. For example, pre-packaged well plates may be provided that a particular configuration of reagent/sample wells, lysing wells, washing wells, elution wells, magnetic bead deposition wells, among other wells associated with a particular purpose.

In some embodiments, a reagent kit and/or well plate kit, may include a set of well plates, where each well plate is filled with a particular solution associated with a particular step or set of steps in nucleic acid extraction. Each well plate in the kit may be loaded into the automated nucleic acid extractor 100 in positions such that the automated nucleic acid extractor 100 may reposition the well plates to locate a well plate of a current step under the magnetic extractor 210. For example, the kit may include five well plates, a lysis well plate for mixing, lysis and extraction of nucleic acids, one or more washing well plates for washing, and an elution well plate for elution, using the lysis well plate to discard the magnetic beads and/or an additional bead well plate for discarding the beads. In some embodiments, the sample being processed may dictate the number of washing steps employed and thus the number of well plates in the kit. In an example, one to three washing steps may be employed between lysis and elution, and thus the kit may be including three to five total well plates. The sample being processed may also dictate the lysis and elution buffers as well as the solutions used for washing. Accordingly, the well plates in the kit may be filled with the buffers and/or solutions associated with lysis, washing and elution of the sample to extract the nucleic acids.

In some embodiments, the kit may include pre-packaged well plates that have been filled in a packaging or manufacturing facility as an off the shelf kit. The operator may then deposit the sample in well of the lysis well plate and load the well plates of the kit in the automated nucleic acid extractor 100. Alternatively, one or more well plates may be filled by the operator manually according to the sample being processed. Any combination of prepackaged and/or manually filled well plates may be employed to form a kit of loading into the automated nucleic acid extractor 100.

In some embodiments, to load the kit into the automated nucleic acid extractor 100, each well plate in the kit may be placed in a well plate carrier 224 in an associated position on the orating platform 220. The operator may place the well plates in pre-defined positions (e.g., a mixing/lysis/extraction position, one or more washing positions, an elution position, etc.), or the operator may place the well plates in any of the positions and define in the program which position is associated with which well plate.

Accordingly, a program associated with a kit may include parameters defining the positions associated with the configuration, such as, e.g., a numerical and/or alphabetical indicator associated with each position on the rotating platform 220, an identifier representing the step of the well plate and/or the solution in well plate, or any combination thereof. Thus, upon implementing the program, the controller 202 may automatically identify from the parameters of each step the positions of each well plate associated with each step.

Therefore, in some embodiments, to perform automated nucleic acid extraction, the operator may insert the well plate into the well plate carrier 224 and select the associated program from the library of programs, e.g., via the display panel 112. In some embodiments, to select the program, the operator may identify a matching identifier to an identifier associated with the kit, inputting an identifier defining the program, selecting a program having a description matching the configuration of the well plates in the kit, configuring the program as a new program, by any other suitable program selection method. In some embodiments, the program may be automatically identified by, e.g., scanning a machine-readable indicium on one or more plates of the reagent kit and/or well plate kit, such as, e.g., a barcode, quick reference (QR) code, numerical code, or other suitable indicia. The control device 110 may receive data represented by the machine-readable indicia and decode the identifier of reagent kit and/or well plate kit. Using the identifier, the control device 110 may identify the associated program in the library.

As a result, the operator may quickly and reliably configure the automated nucleic acid extractor 100 to extract nucleic acids from a sample via selection of a single program associated with sample and/or reagent and/or configuration of wells. Such a software-defined program in a fully automated device enables nucleic acid extraction processes that are repeatably and precisely performed with the same steps and parameters every time. Accordingly, error is reduced, and sample processing time is reduced.

In some embodiments, the operator may configure the program from scratch. In some embodiments, the program may be predefined and may be editable by the operator such that the operator may select the program and modify one or more parameters of one or more steps. In some embodiments, a program may be paired with a reagent kit and/or well plate, e.g., by associating a record of the program with a kit identifier. In some embodiments, the kit identify may identify a kit record in the memory 206 that includes kit parameters defining an associated sample, reagent, regions of the array of wells associated with the positions for lysing, washing, extracting, magnetic bead deposition, etc. Thus, an operator may insert a well plate into the well plate carrier 224 and select via the display panel 112 the kit identifier associated with the well plate to call a predefined program. The controller 202 may utilize the predefined program to control each component of the automated nucleic acid extractor 100 according to the parameters of each step of the program.

In some embodiments, a program may include parameters for mixing a reagent and/or magnetic beads with the sample. Such mixing parameters may include, e.g., mixing wells position, mixing duration, agitation frequency of the magnetic rods 212, agitation amplitude of the magnetic rods 212, mixing temperature, among other parameters or any suitable combination thereof. Accordingly, during the mixing step, the program may control the heating element 222, actuator 216, magnet carrier 214 and/or magnet bars 212 according to the mixing parameters to perform mixing in the mixing wells for the associated duration at the associated temperature.

In some embodiments, a program may include parameters for lysing the sample. Such lysing parameters may include, e.g., lysing wells position, lysing duration, agitation frequency of the magnetic rods 212, agitation amplitude of the magnetic rods 212, lysing temperature, among other parameters or any suitable combination thereof. Accordingly, during the lysing step, the program may control the heating element 222, actuator 216, magnet carrier 214 and/or magnet bars 212 according to the lysing parameters to perform lysing in the lysing wells for the associated duration at the associated temperature.

In some embodiments, a program may include parameters for extracting the magnetic beads with nucleic acids using the magnetic rods 214. Such extraction parameters may include, e.g., attracting duration indicative of a duration for the magnetic rods 214 to maintain position in the lysing wells position to attract the magnetic beads, among other parameters. Accordingly, during the lysing step, the program may control the heating element 222, actuator 216, magnet carrier 214 and/or magnet bars 212 according to the lysing parameters to perform lysing in the lysing wells for the associated duration at the associated temperature.

In some embodiments, a program may include parameters for washing the magnetic rods 214 and magnetic beads. Such washing parameters may include, e.g., washing wells position, washing duration, agitation frequency of the magnetic rods 212, agitation amplitude of the magnetic rods 212, washing temperature, among other parameters or any suitable combination thereof. Accordingly, during the washing step, the program may control the heating element 222, actuator 216, magnet carrier 214 and/or magnet bars 212 according to the washing parameters to perform washing of the magnet bars 212 and/or magnetic beads in the washing wells for the associated duration at the associated temperature.

In some embodiments, a program may include parameters for eluting the nucleic acid from the magnetic beads. Such elution parameters may include, e.g., elution wells position, elution duration, agitation frequency of the magnetic rods 212, agitation amplitude of the magnetic rods 212, elution temperature, among other parameters or any suitable combination thereof. Accordingly, during the elution step, the program may control the heating element 222, actuator 216, magnet carrier 214 and/or magnet bars 212 according to the elution parameters to perform elution to separate the nucleic acid from the magnetic beads in the elution wells for the associated duration at the associated temperature.

In some embodiments, a program may include parameters for removing and depositing the magnetic beads. Such deposition parameters may include, e.g., deposition wells position, attracting duration indicative of a duration for the magnetic rods 214 to maintain position in the lysing wells position to attract the magnetic beads, agitation frequency of the magnetic rods 212, agitation amplitude of the magnetic rods 212, among other parameters or any suitable combination thereof. Accordingly, during the deposition step, the program may control the actuator 216, magnet carrier 214 and/or magnet bars 212 according to the deposition parameters to deposit the magnetic beads in the deposition wells.

In some embodiments, a program may include parameters for disinfecting the interior 130. Such disinfecting parameters may include, e.g., disinfecting temperature, airflow parameters indicative of a speed and a volume of air flow (e.g., via a vent component controlled by the controller 202), a UV irradiation duration, a UV irradiation intensity, among other parameters or any suitable combination thereof. Accordingly, during the disinfecting step, the program may control the heating element 222, a fan/vent, and/or the UV lamps 250 according to the disinfecting parameters to perform disinfecting in the interior 130 for the associated duration at the associated temperature.

Figure 3:
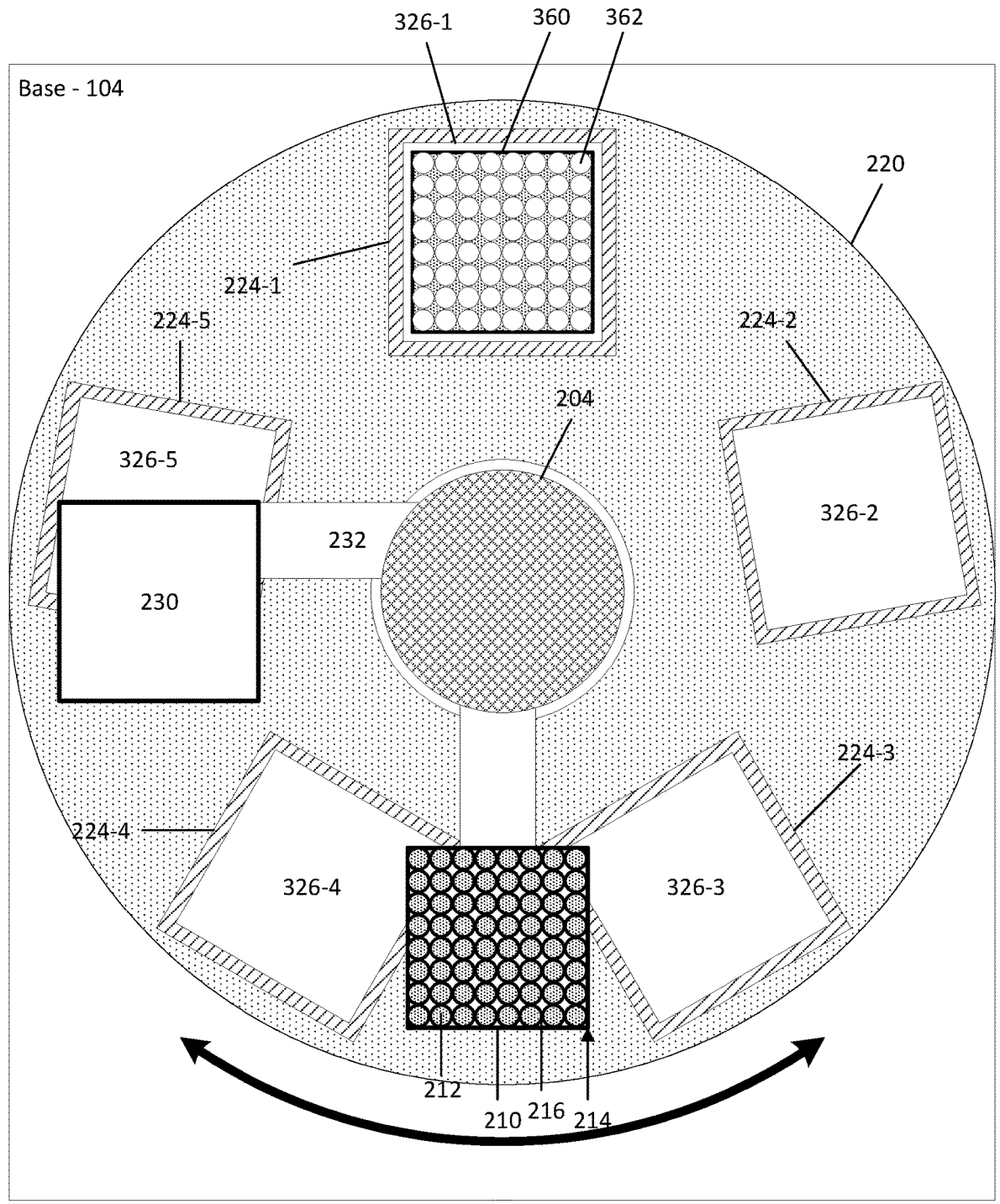
FIG. 3 depicts a top-down interior view of components of the automated nucleic acid extractor for inserting one or more samples and automatically performing nucleic acid extraction on the one or more samples according to one or more programs in accordance with one or more embodiments of the present disclosure.

Referring to FIG. 3, a top-down interior view is illustrated of components of the automated nucleic acid extractor for inserting one or more samples and automatically performing nucleic acid extraction on the one or more samples according to one or more programs in accordance with one or more embodiments of the present disclosure.

In some embodiments, the rotating platform 220 may include multiple well plate carriers 224-1, 224-2, 224-3, 224-4 through 224-5. In some embodiments, the FIG. 3 depicts an embodiment having five well plate carriers 224 associated with five sample processing positions, though any suitable number of sample processing positions may be implemented to enable positioning of a well plate for processing a sample at each step in a program. While the controller 202 controls the components of the automated nucleic acid extractor 100, each step may be associated with a particular sample processing position. Thus, the controller 202 may control the motor 240 to move a well plate 360 into the sample processing position associated with the step being performed, for example into position under the magnetic extractor 210.

In some embodiments, to secure the well plate 360 in a well plate carrier 224-1, the well plate carrier 224-1 may include well plate receiver 326-1 that is shaped to receive the well plate 360 and secure the well plate 360 in place. In some embodiments, the well plate receiver 326-1 may include, e.g., one or more sidewalls, recesses into the platform, detents, positioning pins, brackets, clamps, clasps, hooks, among other retaining mechanisms to hold the well plate 360 in place on the rotating platform 220. In some embodiments, the retaining mechanisms may be fastened, adhered, and/or integrated into the rotating platform 220. In some embodiments, each well plate carrier 224-1, 224-2, 224-3, 224-4, 224-5 may include an associated well plate receiver 326-1, 326-2, 326-3, 326-4, 326-5, respectively.

In some embodiments, as described above, the well plate 360 may include multiple wells 362. The wells 362 may be fastened, adhered, and/or integrated into the well plate 360. In some embodiments, the wells 362 may be arranged in a standardized array, e.g., a predefined number of columns and rows. Accordingly, each well 362 can be indexed according to location within the array. Thus, the controller 202 may locate each well 362 and each position on the well plate according to the indices of each well 362 and each position, e.g., as defined by row and column indexes or any other suitable indexing technique. Accordingly, complicated computer vision and sensing techniques can be avoided by utilizing a common array indexing framework for the well plate 360 and for the controller 202. For example, to extend the magnetic rods 212 into a particular position (e.g., a lysing position or other position), the controller 202 may identify the indices of the lysing wells on the well plate 360, e.g., according to the kit identifier, user selection or other position determination technique. Thus, the program can be efficiently and repeatably performed with reduced risk of error.

In some embodiments, a separate well plate may be loaded in each well plate carrier 224-1, 224-2, 224-3, 224-4, 224-5, for example to process five well plates automatically. Thus, the operator may load the five well plates and define for each well plate an associated program. In some embodiments, the program for each well plate may be the same or different. The controller 202 may then orchestrate the components of the automated nucleic acid extractor 100 to process all five well plates without additional instruction by the operator.

In some embodiments, the controller 202 may process each well plate serially (e.g., complete the processing of one before moving on to the next). Alternatively, or in combination, the controller 202 may process the well plates alternatingly or in parallel. For example, the parameters of one or more steps may include a wait period, heating period, reaction period or other suitable passive period where the magnetic extractor 210 is not actively processing the samples. During such a passive period, the controller 202 may control the motor 240 to reposition the samples to another sample processing position to bring another well plate into position under the magnetic extractor 210 to initiate processing. Accordingly, processing the samples may be performed more efficiently and reliably.

Figure 4:
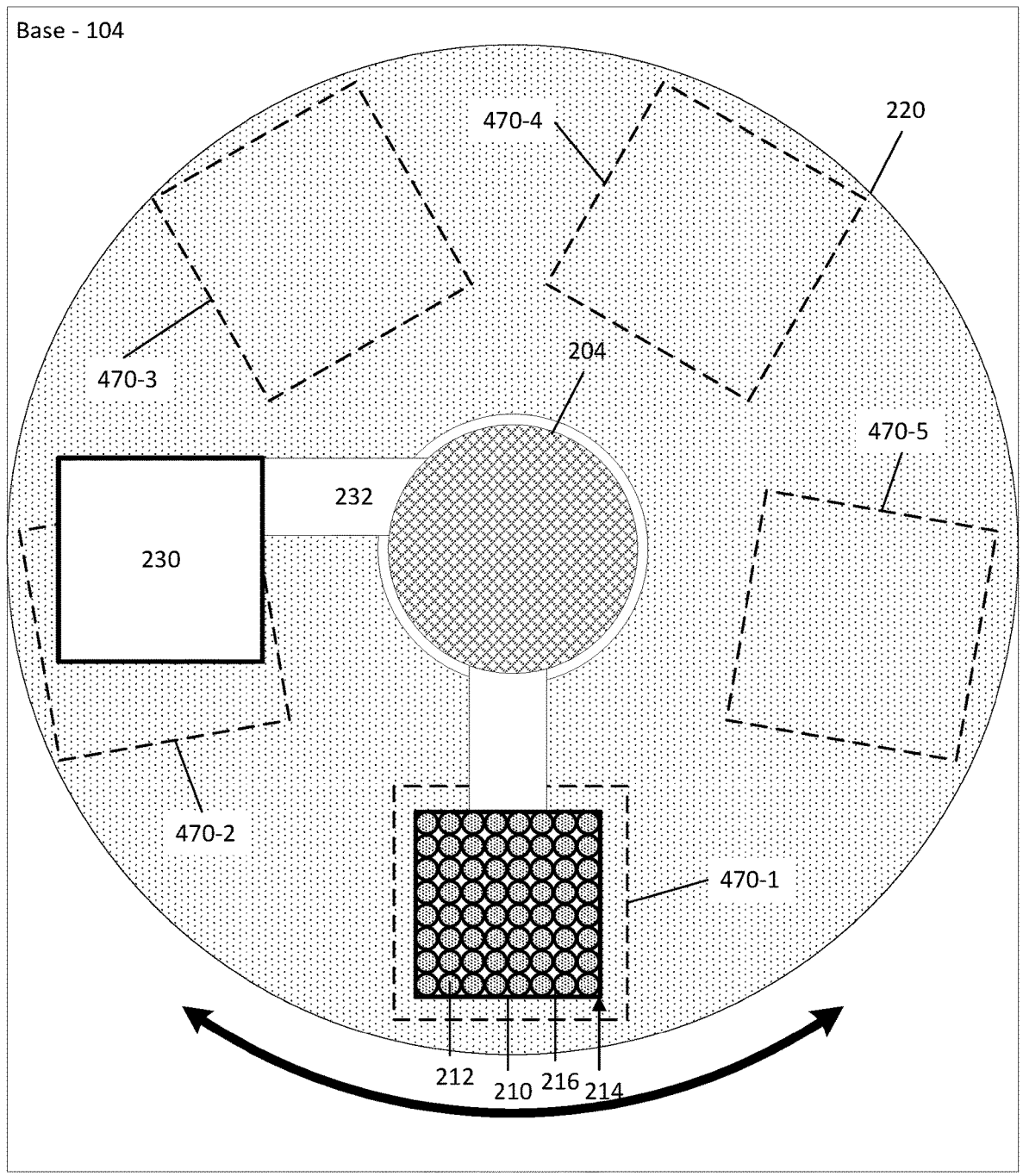
FIG. 4 depicts another top-down interior view of components and positions of the automated nucleic acid extractor for inserting one or more samples and automatically performing nucleic acid extraction on the one or more samples in accordance with one or more embodiments of the present disclosure.

Referring to FIG. 4, another top-down interior view is illustrated of components and positions of the automated nucleic acid extractor for inserting one or more samples and automatically performing nucleic acid extraction on the one or more samples in accordance with one or more embodiments of the present disclosure.

In some embodiments, the rotating platform 220 may include multiple sample processing positions 470-1, 470-2, 470-3, 470-4, 470-5. In some embodiments, the FIG. 4 depicts an embodiment having five sample processing positions 470-1, 470-2, 470-3, 470-4, 470-5, though any suitable number of sample processing positions may be implemented to enable positioning of a well plate for processing a sample at each step in a program. While the controller 202 controls the components of the automated nucleic acid extractor 100, each step may be associated with a particular sample processing position. Thus, the controller 202 may control the motor 240 to move a well plate 360 into the sample processing position associated with the step being performed, for example into position under the magnetic extractor 210. For example, for lysing, attraction, magnetic bead extraction and/or any other steps implementing the magnetic extractor 210, the controller 202 may control the motor 240 to rotate the rotating platform 220 to bring the well plate (e.g., well plate 360), into a first sample processing position 470-1 under the magnetic extractor 210.

Figure 5:
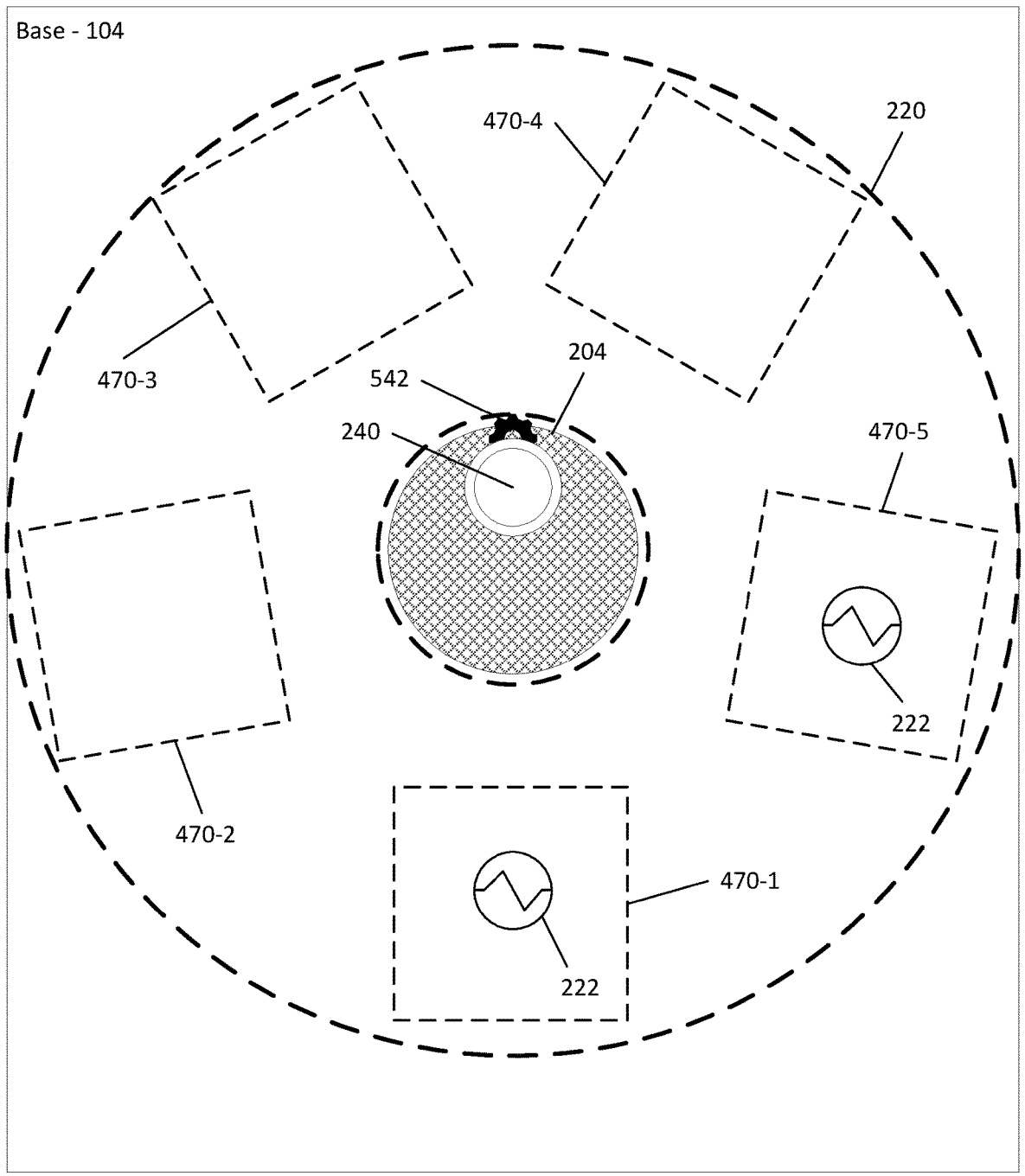
FIG. 5 depicts another top-down interior view of components and positions of the automated nucleic acid extractor for inserting one or more samples and automatically performing nucleic acid extraction on the one or more samples in accordance with one or more embodiments of the present disclosure.

Referring to FIG. 5, another top-down interior view is illustrated of components and positions of the automated nucleic acid extractor for inserting one or more samples and automatically performing nucleic acid extraction on the one or more samples in accordance with one or more embodiments of the present disclosure.

In some embodiments, the rotating platform 220 may include multiple sample processing positions 470-1, 470-2, 470-3, 470-4, 470-5. In some embodiments, the FIG. 5 depicts an embodiment having five sample processing positions 470-1, 470-2, 470-3, 470-4, 470-5, though any suitable number of sample processing positions may be implemented to enable positioning of a well plate for processing a sample at each step in a program. While the controller 202 controls the components of the automated nucleic acid extractor 100, each step may be associated with a particular sample processing position.

In some embodiments, for example, a first sample processing position 470-1 may be associated with steps utilizing the magnetic extractor 210, such as, e.g., mixing, lysing, extraction, washing of the magnetic rods 214 and magnetic beads, elution, and deposition. Thus, for such steps, the controller 202 may utilize the motor 250 to position the well plate (e.g., well plate 360) in the first sample processing position 470-1 under the magnetic extractor 210. In some embodiments, because the aforementioned steps may involve a heating or temperature parameter, the base 104 may include a heating element 222 in the first sample processing position 470-1 such that the controller 202 may control the heating element 222 to implement the temperature parameter of each step in the first sample processing position 470-1.

In some embodiments, a second sample processing position 470-5 may be implemented for warming the reagent and/or sample. Thus, in some embodiments, similar to the first sample processing position 470-1, the base 104 may include a heating element 222 in the second sample processing position 470-5 such that the controller 202 may control the heating element 222 to implement the temperature parameter of each step in the second sample processing position 470-5.

In some embodiments, the automated nucleic acid extractor 100 may include additional sample processing positions 470-2 through 470-4. In some embodiments, the motor 250 may interface with the rotating platform 220 using a drive unit 542 to rotating the rotating platform 240 and position a well plate (e.g., well plate 360) in a particular sample processing position 470-1 through 470-5. In some embodiments, the drive unit 542 may include, e.g., a rotating axle that interfaces with the rotating platform 220 via a gear and/or gear system, via belt drive, via friction at a wheel on the axle, or by any other suitable drive unit 542 enabling the transfer of rotational force from the axle of the motor 240 to the drive the rotation of the rotating platform 220.

In some embodiments, each sample processing position 470-1 through 470-5 may be indexed within the interior 130. Thus, upon loading a well plate, e.g., in the first sample processing position 470-1, the controller 202 may control the motor 240 to position the well plate in the appropriate sample processing position 470-1 through 470-5 according to the indexing. In some embodiments, the controller 202 may use any suitable angular displacement measurement technique to determine the position of the well plate relative to the sample processing positions 470-1 through 470-5. For example, the motor 240 may be controlled to rotate a constant speed such that angular displacement may be determined according a duration of rotation. Alternatively, or in addition, the motor 240 may be a stepper motor where each rotational step corresponds to an angular rotation of the axle. Thus, angular displacement of the rotational platform 220 may be measured by determining the steps of the stepper motor during rotation. Alternatively, or in addition, one or more sensors may be employed to detect the angular displacement, such as, e.g., optical detection of one or more markings on the base 104 and/or the rotating platform 220 and/or the central frame 204, magnetic detection of one or more magnetic markers on the base 104 and/or the rotating platform 220 and/or the central frame 204, radio-frequency identification (RFID) of one or more RFID tags on the base 104 and/or the rotating platform 220 and/or the central frame 204 by one or more RFID readers on the base 104 and/or the rotating platform 220 and/or the central frame 204, or any other suitable technique or any combination thereof.

Figure 6A:
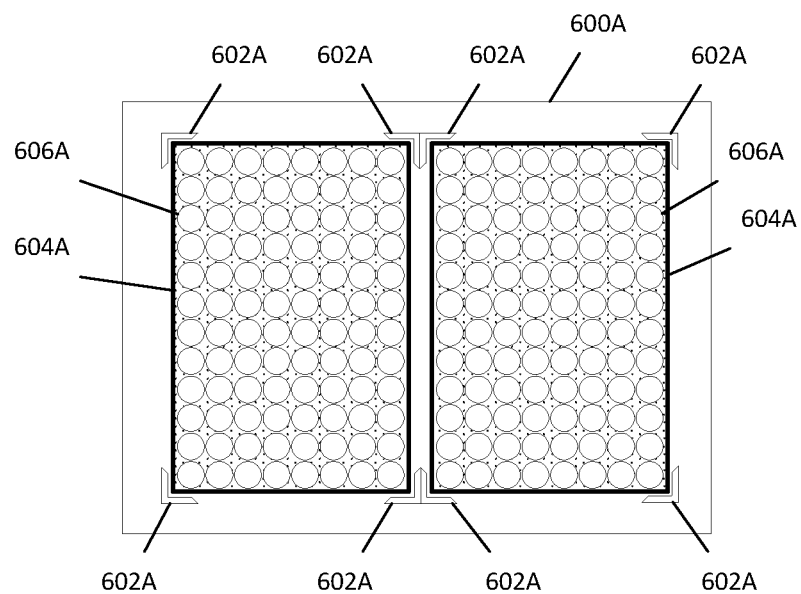
FIG. 6A and FIG. 6B depict example well plate arrangements configured to be received by example well plate carriers in the automated nucleic acid extractor in accordance with one or more embodiments of the present disclosure.
Figure 6B:
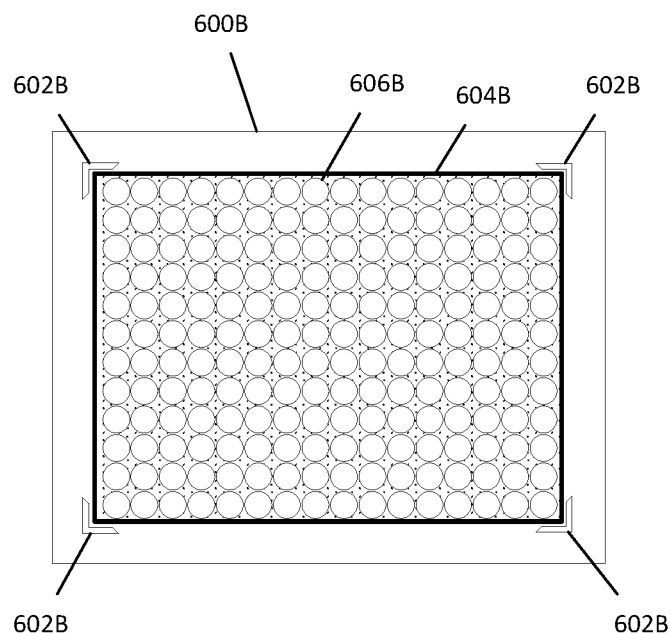

Referring to FIG. 6A and FIG. 6B, example well plate arrangements configured to be received by example well plate carriers in the automated nucleic acid extractor are illustrated in accordance with one or more embodiments of the present disclosure.

In some embodiments, as shown in FIG. 6A, a well plate carrier 600A may accommodate multiple well plates 604A, such as, e.g., two well plates 604A. The well plate carrier 600A may include retention components 602A configured to accept and securing each well plate 604A in position within the well plate carrier 600A. In some embodiments, the retention components 602A may include, e.g., one or more brackets, protrusions, detents, recesses, or other structures or any combination thereof configured to mate with the well plate and secure the well plate in position on the rotating platform 220.

In some embodiments, each well plate 604A may include an array of wells 606A. In some embodiments, FIG. 6A depicts a 96-well plate having an eight by twelve array. In some embodiments, the steps of program as described above may be implemented using positions on the well plate for different processing steps. Each position may be preloaded with compounds, fluids, reagents, solvents, enzymes, etc. for performing the associated step. As a result, the well plate 604A may be configured to operate as a predefined kit with the automated nucleic acid extractor 100 such that the controller 202 may automatically and reliable locate the positions on the well plate for use with each step of a program. In some embodiments, by accommodating two 96-well plates 604A, the automated nucleic acid extractor 100 may process with two kits concurrently. In some embodiments, the magnetic extractor 214 may have two separately controllable magnetic rods 212 and/or magnet carriers 214, each of the two separately controllable magnetic rods 212 and/or magnet carriers 214 being associated with one of the two 96-well plates 604A.

In some embodiments, as shown in FIG. 6B, a well plate carrier 600B may accommodate a single well plate 604B that is double the size of a standard 96-well plate. The well plate carrier 600B may include retention components 602B configured to accept and securing the well plate 604B in position within the well plate carrier 600B. In some embodiments, the retention components 602B may include, e.g., one or more brackets, protrusions, detents, recesses, or other structures or any combination thereof configured to mate with the well plate and secure the well plate in position on the rotating platform 220.

In some embodiments, the well plate 604B may include an array of wells 606B. In some embodiments, FIG. 6B depicts a 192-well plate having a sixteen by twelve array. In some embodiments, the steps of program as described above may be implemented using positions on the well plate for different processing steps. Each position may be preloaded with compounds, fluids, reagents, solvents, enzymes, etc. for performing the associated step. In some embodiments, there may be eight positions. Thus, the 192-well plate may be prepackaged with double the samples to form eight positions of two array columns each (e.g., 24 wells each), thus doubling the processing capacity with a single well plate 604B.

As a result, the well plate 604B may be configured to operate as a predefined kit with the automated nucleic acid extractor 100 such that the controller 202 may automatically and reliable locate the positions on the well plate for use with each step of a program. In some embodiments, the magnetic extractor 214 may have one set of magnetic rods 212 and/or a single magnet carrier 214 associated with one of the one 192-well plates 604A.

Figure 7:
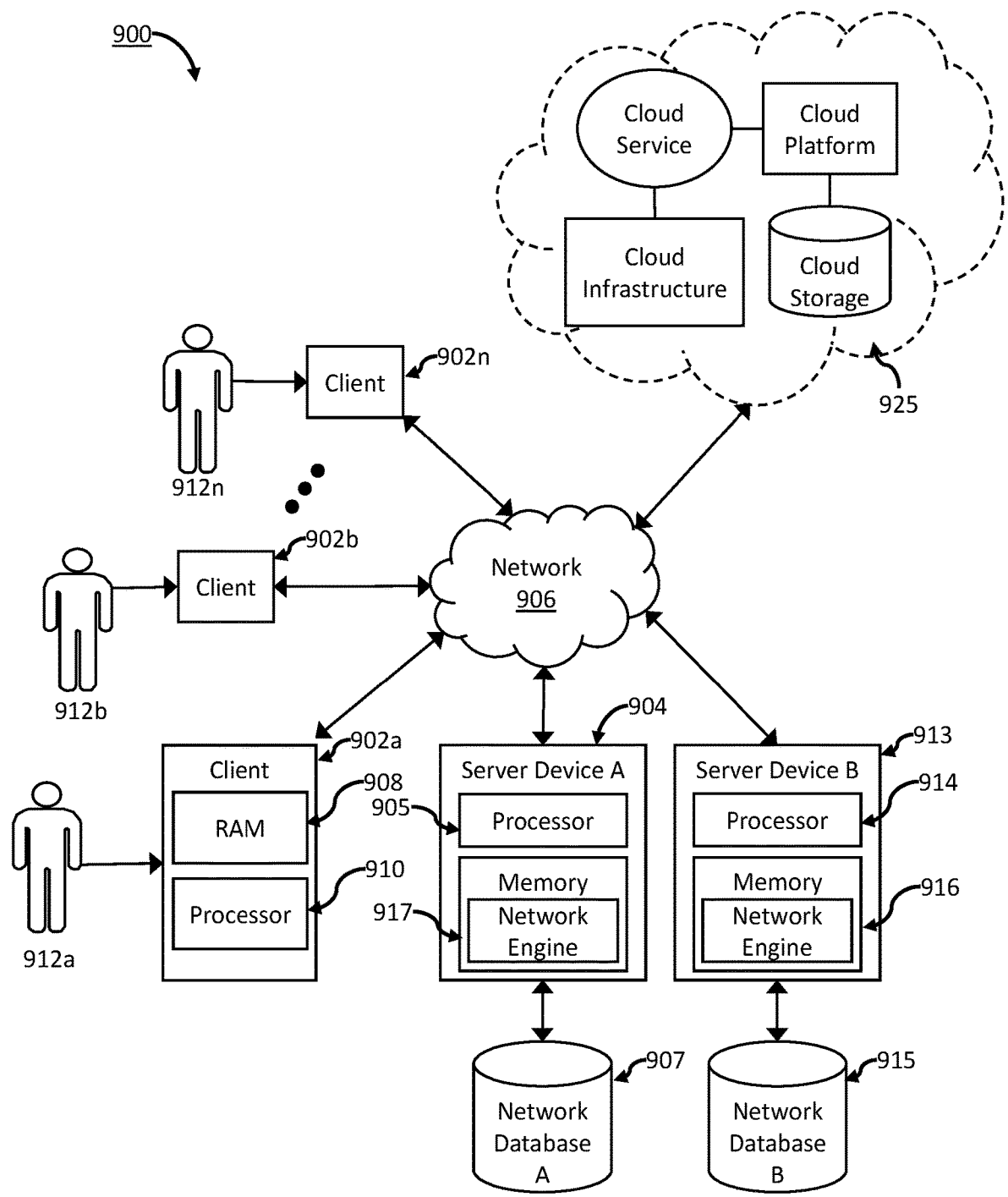
FIG. 7 depicts a block diagram of an exemplary computer-based system and platform for implementing an automated nucleic acid extractor in accordance with one or more embodiments of the present disclosure.

FIG. 7 depicts a block diagram of an exemplary computer-based system and platform 700 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the automated nucleic acid extractor 80 may be a part of, include or otherwise be in communication with a client device 702a, client device 702b through client device 702n, each of which at least includes a computer-readable medium, such as a random-access memory (RAM) 708 coupled to a processor 710 or FLASH memory. In some embodiments, the processor 710 may execute computer-executable program instructions stored in memory 708. In some embodiments, the processor 710 may include a microprocessor, an ASIC, and/or a state machine. In some embodiments, the processor 710 may include, or may be in communication with, media, for example computer-readable media, which stores instructions that, when executed by the processor 710, may cause the processor 710 to perform one or more steps described herein. In some embodiments, examples of computer-readable media may include, but are not limited to, an electronic, optical, magnetic, or other storage or transmission device capable of providing a processor, such as the processor 710 of client device 702a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape, or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may include code from any computer-programming language, including, for example, C, C++, Visual Basic, Java, Python, Perl, JavaScript, etc.

In some embodiments, the client devices 702a through 702n may also include a number of external or internal devices such as a mouse, a CD-ROM, DVD, a physical or virtual keyboard, a display, or other input or output devices. In some embodiments, examples of client devices 702a through 702n (e.g., clients) may be any type of processor-based platforms that are connected to a network 706 such as, without limitation, personal computers, digital assistants, personal digital assistants, smart phones, pagers, digital tablets, laptop computers, Internet appliances, and other processor-based devices. In some embodiments, client devices 702a through 702n may be specifically programmed with one or more application programs in accordance with one or more principles/methodologies detailed herein. In some embodiments, client devices 702a through 702n may operate on any operating system capable of supporting a browser or browser-enabled application, such as Microsoft™, Windows™, and/or Linux. In some embodiments, client devices 702a through 702n shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 702a through 702n, user 712a, user 712b through user 712n, may communicate over the exemplary network 706 with each other and/or with other systems and/or devices coupled to the network 706. As shown in FIG. 7, exemplary server devices 704 and 713 may include processor 705 and processor 714, respectively, as well as memory 717 and memory 716, respectively. In some embodiments, the server devices 704 and 713 may be also coupled to the network 706. In some embodiments, one or more client devices 702a through 702n may be mobile clients.

In some embodiments, at least one database of exemplary databases 707 and 715 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 8:
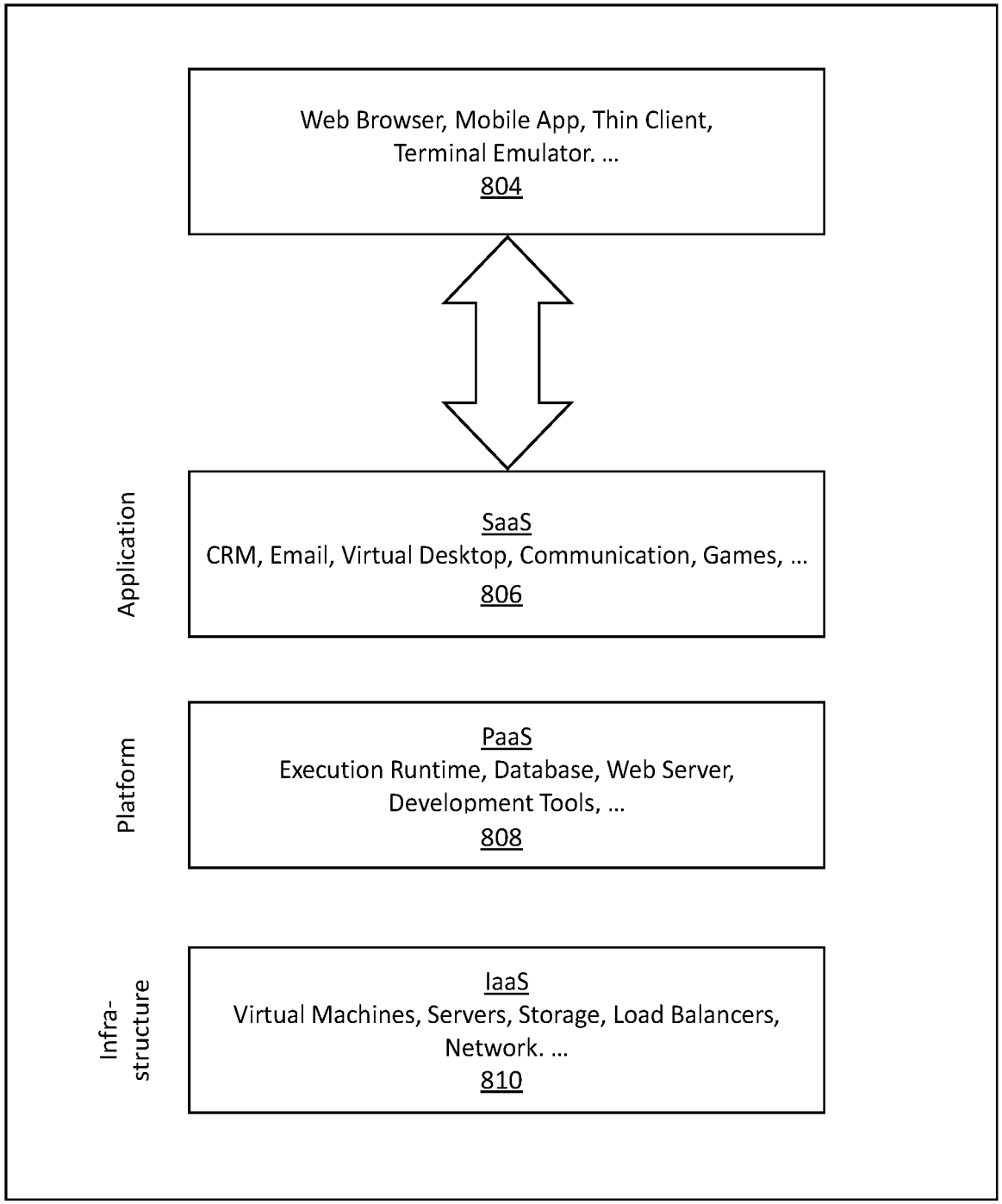
FIG. 8 depicts illustrative schematics of another exemplary implementation of the cloud computing/architecture(s) in which embodiments of a system for automated nucleic acid extraction may be specifically configured to operate in accordance with some embodiments of the present disclosure.

In some embodiments, the exemplary inventive computer-based systems/platforms, the exemplary inventive computer-based devices, and/or the exemplary inventive computer-based components of the present disclosure may be specifically configured to operate in a cloud computing/architecture 725 such as, but not limiting to: infrastructure a service (IaaS) 810, platform as a service (PaaS) 808, and/or software as a service (SaaS) 806 using a web browser, mobile app, thin client, terminal emulator or other endpoint 804. FIG. 8 illustrates schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

Figure 9:
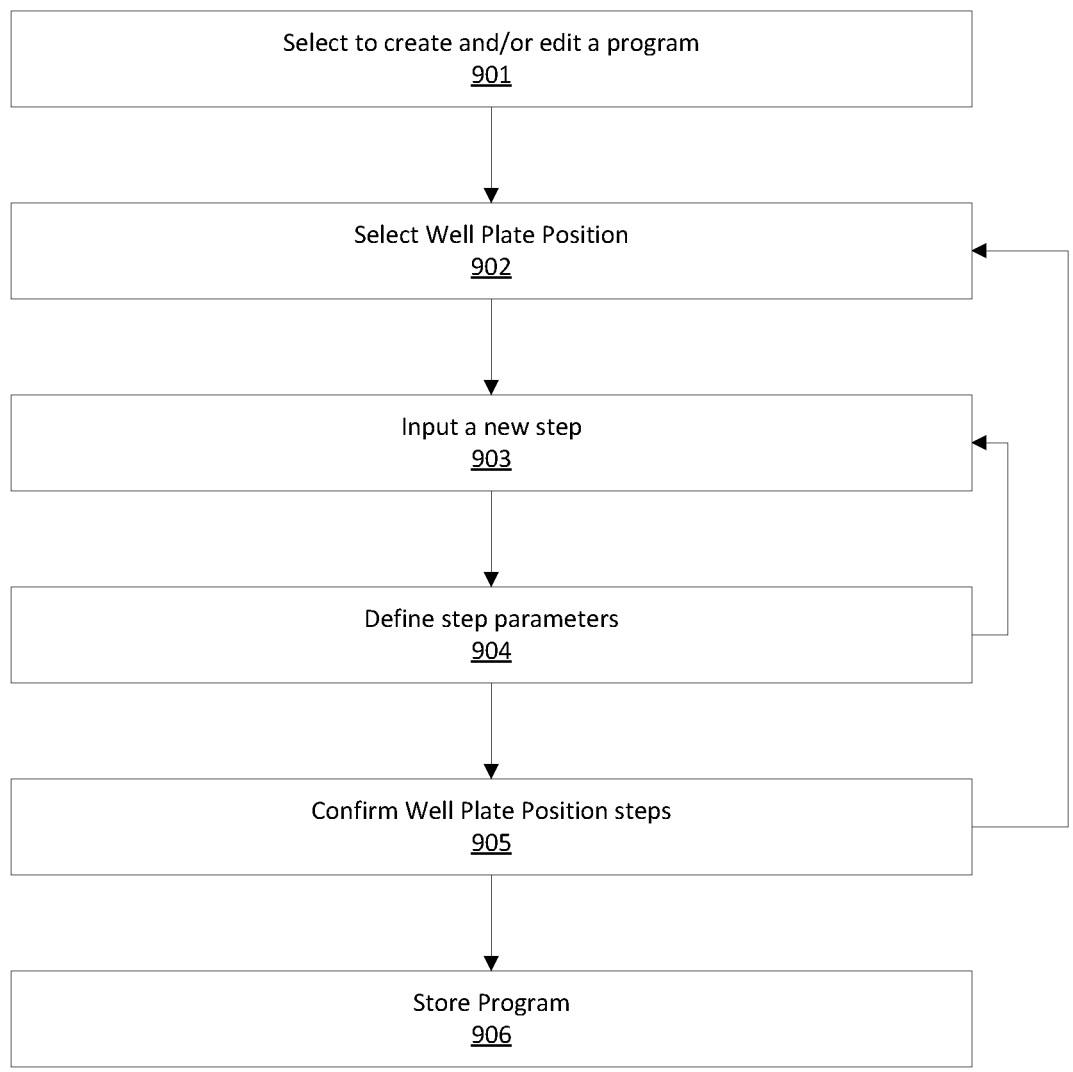
FIG. 9 depicts a flow diagram for creating a program for automated nucleic acid extraction in accordance with one or more embodiments of the present disclosure.

Referring to FIG. 9, a flow diagram for creating a program for automated nucleic acid extraction is depicted in accordance with one or more embodiments of the present disclosure.

At block one, a user may select to create and/or edit a program. For example, the user may navigate a user interface of the control device 110 to interact with a program wizard. In some embodiments, the program wizard may include one or more user interface elements to select to create a program and/or one or more user interface elements to select to edit a program.

In some embodiments, upon selecting to create a new program, the program wizard may cause the user interface to present a set of options and input fields for selecting steps of the program and/or parameters of each step (e.g., time duration, iterations, agitation, agitation frequency, agitation amplitude, temperature, heating time duration, etc.). Each step may be associated with a particular position on the rotating platform 220 and/or a particular well plate at the particular position where the rotating platform 220 accommodates multiple well plates at each position (see, for example, FIG. 6B).

In some embodiments, where the user selects to edit a program, the program wizard may cause the user interface to present a set of stored programs, e.g., labeled by name, sample, sample type, well plate kit identifier, type of sample, or by any other suitable indexing topology or any combination thereof. In some embodiments, the program wizard, in response to a user selection of a program in the set of stored programs, may cause the user interface to present the set of options and input fields for the program and/or parameters of each step with one or more of the set of options and input fields prepopulated with predefined values.

At step 902, the user may customize the program, whether new or stored, by selecting a well plate position for a particular processing step. The well plate position refers to the position on the rotating platform 220 at which the well plate for the particular processing step is intended to be performed.

At step 903, the user may then input a new step that is to occur at the selected well plate position for the well plate. The new step may include, e.g., lysing, mixing, washing, eluting, etc. as detailed above.

At step 904, the user may be, for the new step, define parameters of the step (e.g., time duration, iterations, agitation, agitation frequency, agitation amplitude, temperature, heating time duration, etc.) for processing the well plate at the particular position to effectuate the new step of the program.

In some embodiments, upon selecting each individual parameter, the user may move on to the next parameter of the new step until all parameters have been defined for the new step. In some embodiments, the program wizard may present the options and/or input fields for each parameter of the new step as a group such that the user can select each option and/or input field to input the value. In some embodiments, the program wizard may sequentially present each option and/or input field for the parameters of the new step such that upon the user entering a value for a first option and/or input field, the program wizard may present a second option and/or input field, and then a third, and so on until all parameters of the new step have been defined.

Similarly, in some embodiments, the program wizard may return to step 903 upon all parameters for the new step being defined. Thus, the process for defining the new step may be repeated with a next step in the program until all steps in the program have been defined. In some embodiments, all steps may be defined when a predefined sequence of steps have parameters defined, and/or upon user selection of an interface element to end adding new steps.

At step 905, the user may be presented with an option to confirm the well plate position steps for the program for the selected position. Confirming the steps may cause the program wizard to return to step 902 to enable the user to select another position for which to define the steps and parameters of each step for processing the sample. The process for defining the steps and/or parameters at each position may be repeated until all positions in the program have been defined. In some embodiments, all positions may be defined when a predefined set of positions have the respective steps and/or parameters defined, and/or upon user selection of an interface element to end adding new positions.

At step 906, upon the user completing the parameters for each step of each position in the program, the control device 110 may store the program for later access and execution.

Figure 10:
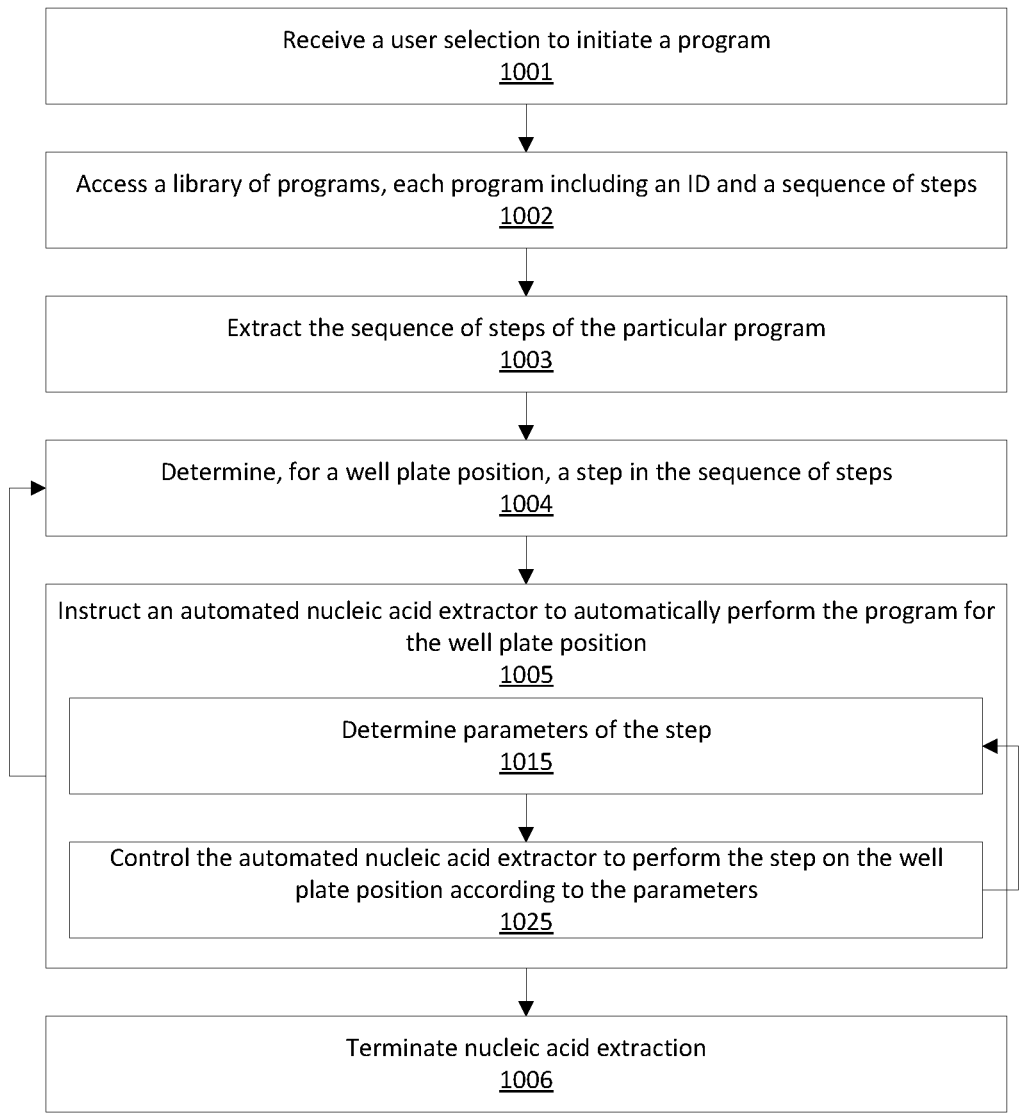
FIG. 10 depicts a flow diagram for controlling the automated nucleic acid extractor 100 according to a program for automated nucleic acid extraction in accordance with one or more embodiments of the present disclosure.

Referring to FIG. 10, a flow diagram for controlling the automated nucleic acid extractor 100 according to a program for automated nucleic acid extraction is depicted in accordance with one or more embodiments of the present disclosure.

At step 1001, the user may select to initiate a program via a user interface of the control device 110. Accordingly, the controller 202 may receive the user's selection of the program. The program may define the steps to be performed at each position on the rotating platform 220 and/or for each well plate in a well plate kit. In some embodiments, the user may select the program from a set of stored programs, e.g., labeled by name, sample, sample type, well plate kit identifier, type of sample, or by any other suitable indexing topology or any combination thereof. Thus, the program may be associated with a particular sample and/or well plate kit.

At step 1002, the controller 202 may access a library storing the set of programs, where each program is indexed according to the indexing topology.

At step 1003, the controller 202 may extract the sequence of steps for the selected program, including the parameters of each step.

At step 1004, the controller 202 may associated each step of the program with a well-plate position on the rotating platform 220 according to a position identifier of each step. In some embodiments, each position may be pre-coded to a particular step, in which case the position identifier may be omitted, and the position may be identified directly by the step.

At step 1005, the controller 202 may instruct the automated nucleic acid extractor 100 to automatically perform the program for the well plate position. To do so, the controller 202 may use the parameters of each step for control the components of the automated nucleic acid extractor 100 to manipulate the sample to perform each step in automated nucleic acid extraction according to, e.g., sub-steps 1015 and 1025.

At step 1015, the controller 202 may identify the parameters of a current step, e.g., by extracting the values of each option and/or input field defining the parameters of each step, e.g., as detailed above. The parameters may include, e.g., time duration, iterations, agitation, agitation frequency, agitation amplitude, temperature, heating time duration, etc.

At step 1025, based upon the parameters of the current step, the controller 202 may control each component of the automated nucleic acid extractor 100 to perform the step including positioning of the well-plates and control of the magnetic extractor according to the parameters, e.g., as detailed above. Upon completion of the step according to the parameters, the controller 202 may return to step 1015 to begin the next step until all steps in the program have been performed.

At step 1006, upon completion of a final step in the program, the controller 202 may terminate nucleic acid extraction. In some embodiments, terminating the nucleic acid extraction may include, e.g., actuating the latch 124 to enable the user to open the door 120 and remove the sample. In some embodiments, terminating the nucleic acid extraction may include, e.g., operating the UV lamps 250 to disinfect the interior of the automated nucleic acid extractor 100 and/or any well-plates remaining inside the automated nucleic acid extractor 100. Similarly, in some embodiments, terminating the nucleic acid extraction may include, e.g., operating a fan and/or vent to vent gases and/or fumes from the interior of the automated nucleic acid extractor 100 and/or any well-plates remaining inside the automated nucleic acid extractor 100.

In some embodiments, the automated nucleic acid extractor may be configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes.

In some embodiments, the automated nucleic acid extractor may employ software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical, or other forms of propagated signals (e.g., carrier waves, infrared signals, digital signals, etc.), and others.

In some embodiments, the automated nucleic acid extractor may employ one or more "computer engines" including at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) FreeBSD, NetBSD, OpenBSD; (2) Linux; (3) Microsoft Windows™; (4) OpenVMS™; (5) OS X (MacOS™); (6) UNIX™; (7) Android; (8) iOS™; (9) Embedded Linux; (10) Tizen™; (11) WebOS™; (12) Adobe AIR™; (13) Binary Runtime Environment for Wireless (BREW™); (14) Cocoa™ (API); (15) Cocoa™ Touch; (16) Java™ Platforms; (17) JavaFX™; (18) QNX™; (19) Mono; (20) Google Blink; (21) Apple WebKit; (22) Mozilla Gecko™; (23) Mozilla XUL; (24) .NET Framework; (25) Silverlight™; (26) Open Web Platform; (27) Oracle Database; (28) Qt™; (29) SAP NetWeaver™; (30) Smartface™; (31) Vexi™; (32) Kubernetes™ and (33) Windows Runtime (WinRT™) or other suitable computer platforms or any combination thereof. In some embodiments, illustrative computer-based systems or platforms of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

At least some aspects of the present disclosure will now be described with reference to the following numbered clauses.

1. A method including:
 receiving, by a controller, a well plate kit indicator indicative of a plurality of well plates and a sample;
  where each well plate in the plurality of well plates is associated with a step in a plurality of steps for extracting nucleic acid from the sample;
  where each well plate is loaded with a particular substance for processing of the sample according to the plurality of steps;
 determining, by the controller, a program associated with the well plate kit indicator;
  where the program includes processing parameters defining at least one instruction for performing each step of the plurality of steps;

determining, by the controller, a plurality of positions on a rotating platform;
  where each position is associated with a well plate of the plurality of well plates;
for each step of the plurality of steps:
  determining, by the controller, a position of the plurality of positions having a well plate of the plurality of well plates for performing each step;
  controlling, by the controller, the rotating platform to position the well plate under a magnetic extractor according to the position of the plurality of positions;
    where the magnetic extractor is mounted to a central frame extending through an axis of the rotating platform;
  controlling, by the controller, at least one actuator associated with the magnetic extractor according to the processing parameters of each step to perform each step on the well plate using a plurality of magnetic rods of the magnetic extractor; and
generating, by the controller upon completion of a final step in the plurality of steps, an alert to an operator that the processing of the sample is complete so as to remove the sample.

2. The method as recited in any of the preceding clauses, further including controlling, by the controller, the rotating platform and the at least one actuator to perform the plurality of steps, including:
determining, by the controller, a position of the plurality of array positions associated with each step;
controlling, by the controller, the magnetic extractor to extend magnetic rods into a first set of wells of a first well plate associated with a first position of the plurality of positions;
controlling, by the controller, the magnetic extractor to perform a mixing step in the first set of wells according to processing parameters associated with the mixing step of the series of steps by actuating the magnetic rods according to at least one first agitation parameter of the mixing step to agitate the sample and cause the sample to mix with the magnetic beads;
  where the magnetic beads are preloaded into the first set of wells;
controlling, by the controller, the magnetic extractor and at least one heating element to perform a lysis step in the first set of wells according to processing parameters associated with the lysis step of the series of steps by:
  actuating the magnetic rods according to at least one second agitation parameter of the lysis step to agitate the sample, and
  heating the heating element according to heating parameters to heat the sample;
controlling, by the controller, the magnetic extractor to perform an extraction step according to processing parameters associated with the extraction step of the series of steps by attracting the magnetic beads to the magnetic rods in the first set of wells;
controlling, by the controller, the magnetic extractor to perform a washing step according to processing parameters associated with the washing step of the series of steps;
  where the processing parameters associated with the washing step are configured cause the controller to extract the magnetic rods from the first set of wells and insert the magnetic rods into a second set of wells of a second well plate in a second position associated with washing the magnetic beads;
controlling, by the controller, the magnetic extractor to perform an elution step according to processing parameters associated with the elution step of the series of steps;
  where the processing parameters associated with the elution step are configured cause the controller to extract the magnetic rods from the second set of wells and insert the magnetic rods into a third set of wells of a third well plate in a third position associated with eluting the nucleic acid from the magnetic beads; and
controlling, by the controller, the magnetic extractor to remove the magnetic rods from the third set of wells to remove the magnetic beads so as to isolate the nucleic acid in the third set of wells.

3. The method as recited in any of the preceding clauses, further including:
controlling, by the controller, the magnetic extractor to perform a deposition step of the series of steps according to processing parameters associated with the deposition step of the series of steps;
  where the series of steps further includes the deposition step for depositing the magnetic beads in the first set of wells;
  where the processing parameters associated with the deposition step are configured cause the controller to control the magnetic extractor to:
    extend the magnetic rods into the first set of wells, and
    agitate the magnetic rods to remove the magnetic beads from the magnetic rods so as to deposit the magnetic beads into the first set of wells.

4. The method as recited in any of the preceding clauses, further including:
controlling, by the controller, at least one ultraviolet lamp to irradiate the magnetic extractor and the rotating platform according to disinfection parameters;
  where the disinfection parameters include an irradiation duration configured to disinfect irradiated surfaces.

5. The method as recited in any of the preceding clauses, further including receiving, by the controller, the processing parameters by user selection via an input interface.

6. The method as recited in any of the preceding clauses, where the well plate kit includes a pre-loaded well kit.

7. The method as recited in any of the preceding clauses, further including:
receiving, by the controller, a second well plate kit indicator indicative of a second plurality of well plates and a second sample;
  where each well plate in the plurality of well plates is associated with a step in a second plurality of steps for extracting a second nucleic acid from the second sample;
  where each well plate is loaded with a particular substance for processing of the sample according to the plurality of steps;
determining, by the controller, a second program associated with the second well plate kit indicator;
  where the second program includes second processing parameters defining at least one second instruction for performing each step of the second plurality of steps;

determining, by the controller, a plurality of second positions on the rotating platform;
  where each second position is associated with a well plate of the second plurality of well plates;
  where each second position is adjacent to a respective position of the plurality of positions so as to enable processing two well plate kits in parallel.

8. The method as recited in any of the preceding clauses, where the magnetic rods include non-magnetic sleeves; and
  where the controller controls the at least one actuator to separately actuate the magnetic rods and the non-magnetic sleeves.

9. The method as recited in any of the preceding clauses, further including controlling, by the controller, a second heater at a second position of the rotating platform to pre-heat at least one well plate of the plurality of well plates.

10. The method as recited in any of the preceding clauses, where each position is associated with two well plates of two well plate kits;
  where the magnetic extractor includes two sets of magnetic rods; and
  where each set of magnetic rods of the two sets of magnetic rods are independently controllable to process a respective well plate of the two well plates of each position.

11. A system including:
  a controller of an automated nucleic acid extractor, where the controller is configured to:
    receive a well plate kit indicator indicative of a plurality of well plates and a sample;
      where each well plate in the plurality of well plates is associated with a step in a plurality of steps for extracting nucleic acid from the sample;
      where each well plate is loaded with a particular substance for processing of the sample according to the plurality of steps;
    determine a program associated with the well plate kit indicator;
      where the program includes processing parameters defining at least one instruction for performing each step of the plurality of steps;
    determine a plurality of positions on a rotating platform;
      where each position is associated with a well plate of the plurality of well plates;
    for each step of the plurality of steps:
      determine a position of the plurality of positions having a well plate of the plurality of well plates for performing each step;
      control the rotating platform to position the well plate under a magnetic extractor according to the position of the plurality of positions;
        where the magnetic extractor is mounted to a central frame extending through an axis of the rotating platform;
      control at least one actuator associated with the magnetic extractor according to the processing parameters of each step to perform each step on the well plate using a plurality of magnetic rods of the magnetic extractor; and
    generate, upon completion of a final step in the plurality of steps, an alert to an operator that the processing of the sample is complete so as to remove the sample.

12. The system as recited in any of the preceding clauses, where the controller is further configured to control the rotating platform and the at least one actuator to perform the plurality of steps, including:
  determine a position of the plurality of array positions associated with each step;
  control the magnetic extractor to extend magnetic rods into a first set of wells of a first well plate associated with a first position of the plurality of positions;
  control the magnetic extractor to perform a mixing step in the first set of wells according to processing parameters associated with the mixing step of the series of steps by actuating the magnetic rods according to at least one first agitation parameter of the mixing step to agitate the sample and cause the sample to mix with the magnetic beads;
    where the magnetic beads are preloaded into the first set of wells;
  control the magnetic extractor and at least one heating element to perform a lysis step in the first set of wells according to processing parameters associated with the lysis step of the series of steps by:
    actuating the magnetic rods according to at least one second agitation parameter of the lysis step to agitate the sample, and
    heating the heating element according to heating parameters to heat the sample;
  control the magnetic extractor to perform an extraction step according to processing parameters associated with the extraction step of the series of steps by attracting the magnetic beads to the magnetic rods in the first set of wells;
  control the magnetic extractor to perform a washing step according to processing parameters associated with the washing step of the series of steps;
    where the processing parameters associated with the washing step are configured cause the controller to extract the magnetic rods from the first set of wells and insert the magnetic rods into a second set of wells of a second well plate in a second position associated with washing the magnetic beads;
  control the magnetic extractor to perform an elution step according to processing parameters associated with the elution step of the series of steps;
    where the processing parameters associated with the elution step are configured cause the controller to extract the magnetic rods from the second set of wells and insert the magnetic rods into a third set of wells of a third well plate in a third position associated with eluting the nucleic acid from the magnetic beads; and
  control the magnetic extractor to remove the magnetic rods from the third set of wells to remove the magnetic beads so as to isolate the nucleic acid in the third set of wells.

13. The system as recited in any of the preceding clauses, where the controller is further configured to:
  control the magnetic extractor to perform a deposition step of the series of steps according to processing parameters associated with the deposition step of the series of steps;
    where the series of steps further includes the deposition step for depositing the magnetic beads in the first set of wells;
    where the processing parameters associated with the deposition step are configured cause the controller to control the magnetic extractor to:

extend the magnetic rods into the first set of wells, and agitate the magnetic rods to remove the magnetic beads from the magnetic rods so as to deposit the magnetic beads into the first set of wells.

14. The system as recited in any of the preceding clauses, where the controller is further configured to:
control at least one ultraviolet lamp to irradiate the magnetic extractor and the rotating platform according to disinfection parameters;
where the disinfection parameters include an irradiation duration configured to disinfect irradiated surfaces.

15. The system as recited in any of the preceding clauses, where the controller is further configured to receive the processing parameters by user selection via an input interface.

16. The system as recited in any of the preceding clauses, where the well plate kit includes a pre-loaded well kit.

17. The system as recited in any of the preceding clauses, where the controller is further configured to:
receive a second well plate kit indicator indicative of a second plurality of well plates and a second sample;
where each well plate in the plurality of well plates is associated with a step in a second plurality of steps for extracting a second nucleic acid from the second sample;
where each well plate is loaded with a particular substance for processing of the sample according to the plurality of steps;
determine a second program associated with the second well plate kit indicator;
where the second program includes second processing parameters defining at least one second instruction for performing each step of the second plurality of steps;
determine a plurality of second positions on the rotating platform;
where each second position is associated with a well plate of the second plurality of well plates;
where each second position is adjacent to a respective position of the plurality of positions so as to enable processing two well plate kits in parallel.

18. The system as recited in any of the preceding clauses, where the magnetic rods include non-magnetic sleeves; and
where the controller controls the at least one actuator to separately actuate the magnetic rods and the non-magnetic sleeves.

19. The system as recited in any of the preceding clauses, where the controller is further configured to control a second heater at a second position of the rotating platform to pre-heat at least one well plate of the plurality of well plates.

20. The system as recited in any of the preceding clauses, where each position is associated with two well plates of two well plate kits;
where the magnetic extractor includes two sets of magnetic rods; and
where each set of magnetic rods of the two sets of magnetic rods are independently controllable to process a respective well plate of the two well plates of each position.

The aforementioned examples are, of course, illustrative and not restrictive.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

What is claimed is:

1. A method comprising:
receiving, by a controller, a well plate kit indicator indicative of a plurality of well plates and a sample;
wherein each well plate in the plurality of well plates is associated with a step in a plurality of steps for extracting nucleic acid from the sample;
wherein each well plate is loaded with a particular substance for processing of the sample according to the plurality of steps;
determining, by the controller, a program associated with the well plate kit indicator;
wherein the program comprises processing parameters defining at least one instruction for performing each step of the plurality of steps;
determining, by the controller, a plurality of positions on a rotating platform;
wherein each position is associated with a well plate of the plurality of well plates;
for each step of the plurality of steps:
determining, by the controller, a position of the plurality of positions having a well plate of the plurality of well plates for performing each step;
controlling, by the controller, the rotating platform to position the well plate under a magnetic extractor according to the position of the plurality of positions;
wherein the magnetic extractor is mounted to a central frame extending through an axis of the rotating platform;
controlling, by the controller, at least one actuator associated with the magnetic extractor according to the processing parameters of each step to perform each step on the well plate using a plurality of magnetic rods of the magnetic extractor; and
generating, by the controller upon completion of a final step in the plurality of steps, an alert to an operator that the processing of the sample is complete so as to remove the sample.

2. The method of claim 1, further comprising controlling, by the controller, the rotating platform and the at least one actuator to perform the plurality of steps, comprising:
determining, by the controller, a position of the plurality of array positions associated with each step;
controlling, by the controller, the magnetic extractor to extend magnetic rods into a first set of wells of a first well plate associated with a first position of the plurality of positions;
controlling, by the controller, the magnetic extractor to perform a mixing step in the first set of wells according to processing parameters associated with the mixing step of the series of steps by actuating the magnetic rods according to at least one first agitation parameter of the mixing step to agitate the sample and cause the sample to mix with the magnetic beads;
wherein the magnetic beads are preloaded into the first set of wells;

controlling, by the controller, the magnetic extractor and at least one heating element to perform a lysis step in the first set of wells according to processing parameters associated with the lysis step of the series of steps by:
  actuating the magnetic rods according to at least one second agitation parameter of the lysis step to agitate the sample, and
  heating the heating element according to heating parameters to heat the sample;
controlling, by the controller, the magnetic extractor to perform an extraction step according to processing parameters associated with the extraction step of the series of steps by attracting the magnetic beads to the magnetic rods in the first set of wells;
controlling, by the controller, the magnetic extractor to perform a washing step according to processing parameters associated with the washing step of the series of steps;
  wherein the processing parameters associated with the washing step are configured cause the controller to extract the magnetic rods from the first set of wells and insert the magnetic rods into a second set of wells of a second well plate in a second position associated with washing the magnetic beads;
controlling, by the controller, the magnetic extractor to perform an elution step according to processing parameters associated with the elution step of the series of steps;
  wherein the processing parameters associated with the elution step are configured cause the controller to extract the magnetic rods from the second set of wells and insert the magnetic rods into a third set of wells of a third well plate in a third position associated with eluting the nucleic acid from the magnetic beads; and
controlling, by the controller, the magnetic extractor to remove the magnetic rods from the third set of wells to remove the magnetic beads so as to isolate the nucleic acid in the third set of wells.

3. The method of claim 1, further comprising:
controlling, by the controller, the magnetic extractor to perform a deposition step of the series of steps according to processing parameters associated with the deposition step of the series of steps;
  wherein the series of steps further comprises the deposition step for depositing the magnetic beads in the first set of wells;
  wherein the processing parameters associated with the deposition step are configured cause the controller to control the magnetic extractor to:
    extend the magnetic rods into the first set of wells, and
    agitate the magnetic rods to remove the magnetic beads from the magnetic rods so as to deposit the magnetic beads into the first set of wells.

4. The method of claim 1, further comprising:
controlling, by the controller, at least one ultraviolet lamp to irradiate the magnetic extractor and the rotating platform according to disinfection parameters;
  wherein the disinfection parameters comprise an irradiation duration configured to disinfect irradiated surfaces.

5. The method of claim 1, further comprising receiving, by the controller, the processing parameters by user selection via an input interface.

6. The method of claim 1, wherein the well plate kit comprises a pre-loaded well kit.

7. The method of claim 1, further comprising:
receiving, by the controller, a second well plate kit indicator indicative of a second plurality of well plates and a second sample;
  wherein each well plate in the plurality of well plates is associated with a step in a second plurality of steps for extracting a second nucleic acid from the second sample;
  wherein each well plate is loaded with a particular substance for processing of the sample according to the plurality of steps;
determining, by the controller, a second program associated with the second well plate kit indicator;
  wherein the second program comprises second processing parameters defining at least one second instruction for performing each step of the second plurality of steps;
determining, by the controller, a plurality of second positions on the rotating platform;
  wherein each second position is associated with a well plate of the second plurality of well plates;
  wherein each second position is adjacent to a respective position of the plurality of positions so as to enable processing two well plate kits in parallel.

8. The method of claim 1, wherein the magnetic rods comprise non-magnetic sleeves; and
  wherein the controller controls the at least one actuator to separately actuate the magnetic rods and the non-magnetic sleeves.

9. The method of claim 1, further comprising controlling, by the controller, a second heater at a second position of the rotating platform to pre-heat at least one well plate of the plurality of well plates.

10. The method of claim 1, wherein each position is associated with two well plates of two well plate kits;
  wherein the magnetic extractor comprises two sets of magnetic rods; and
  wherein each set of magnetic rods of the two sets of magnetic rods are independently controllable to process a respective well plate of the two well plates of each position.

11. A system comprising:
a controller of an automated nucleic acid extractor, wherein the controller is configured to:
  receive a well plate kit indicator indicative of a plurality of well plates and a sample;
    wherein each well plate in the plurality of well plates is associated with a step in a plurality of steps for extracting nucleic acid from the sample;
    wherein each well plate is loaded with a particular substance for processing of the sample according to the plurality of steps;
  determine a program associated with the well plate kit indicator;
    wherein the program comprises processing parameters defining at least one instruction for performing each step of the plurality of steps;
  determine a plurality of positions on a rotating platform;
    wherein each position is associated with a well plate of the plurality of well plates;
  for each step of the plurality of steps:
    determine a position of the plurality of positions having a well plate of the plurality of well plates for performing each step;

control the rotating platform to position the well plate under a magnetic extractor according to the position of the plurality of positions;
  wherein the magnetic extractor is mounted to a central frame extending through an axis of the rotating platform;
control at least one actuator associated with the magnetic extractor according to the processing parameters of each step to perform each step on the well plate using a plurality of magnetic rods of the magnetic extractor; and
generate, upon completion of a final step in the plurality of steps, an alert to an operator that the processing of the sample is complete so as to remove the sample.

12. The system of claim 11, wherein the controller is further configured to control the rotating platform and the at least one actuator to perform the plurality of steps, comprising:
  determine a position of the plurality of array positions associated with each step;
  control the magnetic extractor to extend magnetic rods into a first set of wells of a first well plate associated with a first position of the plurality of positions;
  control the magnetic extractor to perform a mixing step in the first set of wells according to processing parameters associated with the mixing step of the series of steps by actuating the magnetic rods according to at least one first agitation parameter of the mixing step to agitate the sample and cause the sample to mix with the magnetic beads;
    wherein the magnetic beads are preloaded into the first set of wells;
  control the magnetic extractor and at least one heating element to perform a lysis step in the first set of wells according to processing parameters associated with the lysis step of the series of steps by:
    actuating the magnetic rods according to at least one second agitation parameter of the lysis step to agitate the sample, and
    heating the heating element according to heating parameters to heat the sample;
  control the magnetic extractor to perform an extraction step according to processing parameters associated with the extraction step of the series of steps by attracting the magnetic beads to the magnetic rods in the first set of wells;
  control the magnetic extractor to perform a washing step according to processing parameters associated with the washing step of the series of steps;
    wherein the processing parameters associated with the washing step are configured cause the controller to extract the magnetic rods from the first set of wells and insert the magnetic rods into a second set of wells of a second well plate in a second position associated with washing the magnetic beads;
  control the magnetic extractor to perform an elution step according to processing parameters associated with the elution step of the series of steps;
    wherein the processing parameters associated with the elution step are configured cause the controller to extract the magnetic rods from the second set of wells and insert the magnetic rods into a third set of wells of a third well plate in a third position associated with eluting the nucleic acid from the magnetic beads; and
  control the magnetic extractor to remove the magnetic rods from the third set of wells to remove the magnetic beads so as to isolate the nucleic acid in the third set of wells.

13. The system of claim 11, wherein the controller is further configured to:
  control the magnetic extractor to perform a deposition step of the series of steps according to processing parameters associated with the deposition step of the series of steps;
    wherein the series of steps further comprises the deposition step for depositing the magnetic beads in the first set of wells;
    wherein the processing parameters associated with the deposition step are configured cause the controller to control the magnetic extractor to:
      extend the magnetic rods into the first set of wells, and
      agitate the magnetic rods to remove the magnetic beads from the magnetic rods so as to deposit the magnetic beads into the first set of wells.

14. The system of claim 11, wherein the controller is further configured to:
  control at least one ultraviolet lamp to irradiate the magnetic extractor and the rotating platform according to disinfection parameters;
    wherein the disinfection parameters comprise an irradiation duration configured to disinfect irradiated surfaces.

15. The system of claim 11, wherein the controller is further configured to receive the processing parameters by user selection via an input interface.

16. The system of claim 11, wherein the well plate kit comprises a pre-loaded well kit.

17. The system of claim 11, wherein the controller is further configured to:
  receive a second well plate kit indicator indicative of a second plurality of well plates and a second sample;
    wherein each well plate in the plurality of well plates is associated with a step in a second plurality of steps for extracting a second nucleic acid from the second sample;
    wherein each well plate is loaded with a particular substance for processing of the sample according to the plurality of steps;
  determine a second program associated with the second well plate kit indicator;
    wherein the second program comprises second processing parameters defining at least one second instruction for performing each step of the second plurality of steps;
  determine a plurality of second positions on the rotating platform;
    wherein each second position is associated with a well plate of the second plurality of well plates;
    wherein each second position is adjacent to a respective position of the plurality of positions so as to enable processing two well plate kits in parallel.

18. The system of claim 11, wherein the magnetic rods comprise non-magnetic sleeves; and
  wherein the controller controls the at least one actuator to separately actuate the magnetic rods and the non-magnetic sleeves.

19. The system of claim 11, wherein the controller is further configured to control a second heater at a second position of the rotating platform to pre-heat at least one well plate of the plurality of well plates.

20. The system of claim 11, wherein each position is associated with two well plates of two well plate kits;
   wherein the magnetic extractor comprises two sets of magnetic rods; and
   wherein each set of magnetic rods of the two sets of magnetic rods are independently controllable to process a respective well plate of the two well plates of each position.

\* \* \* \* \*